US006864406B1

(12) United States Patent
Botella

(10) Patent No.: US 6,864,406 B1
(45) **Date of Patent: *Mar. 8, 2005**

(54) ACC SYNTHASE GENE

(75) Inventor: Jose Ramon Botella, Kenmore (AU)

(73) Assignee: University of Queensland, Queensland (AU)

( * ) Notice: Subject to any disclaimer, the term of this patent is extended or adjusted under 35 U.S.C. 154(b) by 306 days.

This patent is subject to a terminal disclaimer.

(21) Appl. No.: 09/669,476

(22) Filed: Sep. 25, 2000

Related U.S. Application Data

(63) Continuation of application No. 09/043,627, filed as application No. PCT/AU96/00591 on Sep. 20, 1996, now Pat. No. 6,124,525.

(30) Foreign Application Priority Data

Sep. 20, 1995 (AU) ............................................. PN5559
May 2, 1996 (AU) ............................................. PN9603

(51) Int. Cl.[7] ......................... A01H 5/00; C12N 15/82; C12N 15/52

(52) U.S. Cl. ...................... 800/298; 800/278; 800/283; 800/286; 536/23.2; 536/23.6

(58) Field of Search ................................ 800/278, 298, 800/286, 283; 536/23.2, 23.6; 435/69.1, 320.1, 419, 468

(56) References Cited

U.S. PATENT DOCUMENTS 6,124,525 A * 9/2000 Botella ...................... 800/298

FOREIGN PATENT DOCUMENTS

| WO | 92/12249 | 7/1991 |
|---|---|---|
| WO | 92/04456 | 3/1992 |

OTHER PUBLICATIONS

Robbins et al., Genetic Manipulation of Condensed Tannins in Higher Plants, 1998, Plant Physiol. vol. 116, pp. 1133–1144.*

Krol et al., Inhibition of flowers pigmentation by antisense CHS genes: promoter and minimal sequence requirements for the antisense effect, 1990, Plant Molecular Biology, vol. 14, pp. 457–466.*

Botella et al., "Identification and Characterization of a Full–length cDNA Encoding for Auxin–induced 1–Aminocyclopropane–1–Carboxylate Synthase from Violated Mung Bean Hypocotyl Segments and Expressions of its mRNA in Response to Indole–3–Acetic Acid," Journal of Molecular Biology 20: (1992) 425–436.

Miki et al., "Nucleotide Sequence of a cDNA for 1–Aminocyclopropane–1–Carboxylate Synthase from Melon Fruits," Plant Physiology 107 (1995) 297–298.

Van Der Straeten, et al., "Cloning, Genetic Mapping, and Expression Analysis of an *Arabidopsis thaliana* Gene that Encodes 1–Aminocyclopropane–1–Carboxylate Synthase," Proceedings of National Academy of Science USA 89 (1992) 9969–9973.

Yip, et al., "Differential Accumulation of Transcripts for Four Tomato 1–Aminocyclopropane–1–Carboxylate Synthase Homologs under Various Conditions," Proceedings of National Academy of Science, USA 89 (1992) 2475–2479.

Rottmann, et al., "1–Aminocyclopropane–1–Carboxylate Synthase in Tomato is Encoded by a Multigene Family Whose Transcription is Induced During Fruit and Floral Senescence," Molecular Biology (1991) 937–961.

Olson, et al., "Differential Expression of Two Genes for 1–Aminocyclopropane–1–Carboxylate Synthase in Tomato Fruits," Proceedings of National Academy of Science, USA 88 (1991) 5340–5344.

Plant Gene Expression Center, "One Rotten Apple Spoils the Whole Bushel: The Role of Ethylene in Fruit Ripening," Cell 7 Press (1992) 181–184.

* cited by examiner

*Primary Examiner*—David T. Fox
*Assistant Examiner*—Russell Kallis
(74) *Attorney, Agent, or Firm*—Mathews, Collins, Shepherd & McKay, PA

(57) ABSTRACT

New ACC synthase genes from pineapple, papaya and mango are disclosed which have utility as targets for the generation of transgenic plants in which the expression of ACC synthase is substantially controlled to effect the regulation of plant development, and in particular, fruit ripening.

9 Claims, 10 Drawing Sheets

FIG. 1

```
 Q  M  G  F  A  E  N  Q  L  S  L  E  L  I  R  E  W  I  K  N
CAGATGGGGTTTGCGGAGAACCAGCTTTCGCTGGAGTTAATACGTGAGTGGATCAAGAAT     60

 H  P  E  A  S  I  C  S  A  E  G  L  P  Q  F  M  E  I  A  N
CACCCGGAGGCCTCCATTTGCTCGGCGGAGGGCCTGCCGCAGTTCATGGAGATCGCCAAT    120

 F  Q  D  Y  H  G  L  P  A  F  L  Q  G  I  A  K  L  M  E  K
TTCCAAGACTACCATGGCTTGCCGGCTTTTCTGCAGGGAATCGCGAAATTGATGGAGAAA    180

 V  R  G  G  R  V  K  F  D  P  N  R  V  V  M  S  G  G  G  T
GTGAGAGGAGGAAGGGTCAAATTCGATCCGAACCGCGTGGTGATGAGCGGCGGAGGCACT    240

 G  A  Q  E  T  L  A  F  C  L  A  D  P  G  D  A  F  L  V  P
GGAGCGCAAGAAACGCTCGCGTTTTGTCTCGCTGACCCTGGCGACGCCTTCCTCGTCCCA    300

 T  P  Y  Y  P  A  F  N  R  D  L  R  W  R  T  G  V  E  L  L
ACTCCGTACTATCCAGCATTTAATCGCGATCTCCGGTGGAGAACGGGCGTCGAGCTCCTC    360

 P  V  H  C  K  S  S  N  H  F  R  V  T  K  T  A  L  E  S  A
CCGGTTCACTGCAAGAGCTCTAATCACTTCAGAGTCACCAAAACGGCGCTAGAATCGGCA    420

 Y  E  K  A  R  K  D  N  I  R  V  K  G  V  L  I  T  N  P  S
TACGAGAAGGCGCGAAAGGATAACATCAGAGTAAAAGGAGTACTGATAACCAACCCATCC    480

 N  P  L  G  T  T  M  D  K  H  T  L  Q  T  L  V  K  F  V  N
AACCCGCTCGGCACGACCATGGATAAACACACGCTACAGACCCTCGTGAAATTCGTAAAC    540
```

FIG. 1 cont'd

```
 E  R  R  I  H  L  V  C  D  E  L  Y  G  A  T  I  F  R  E  P
GAAAGGAGAATCCACCTAGTCTGCGACGAGTTATACGGCGCAACCATCTTTAGGGAGCCC    600

 R  F  V  S  I  S  E  V  I  E  E  D  P  N  C  D  K  N  L  I
AGGTTCGTCAGCATCTCCGAGGTAATAGAAGAGGACCCGAACTGCGACAAGAATCTGATC    660

 H  I  A  Y  S  L  S  K  D  F  G  L  P  G  F  R  V  G  I  V
CACATTGCGTACAGTCTCTCAAAGGACTTCGGTCTCCCCGGATTCCGAGTCGGGATCGTG    720

 Y  S  Y  N  D  T  V  V  S  C  A  R  R  M  S  S  F  G  L  V
TATTCCTACAACGACACGGTGGTTAGTTGCGCACGCAGAATGTCGAGCTTCGGCCTCGTC    780

 S  S  Q  T  Q  Y  L  L  A  A  M  L  S  G  E  E  F  L  P  T
TCGTCGCAGACACAGTACCTACTGGCCGCCATGCTATCCGGCGAAGAATTTTTGCCAACA    840

 L  L  T  E  S  A  K  S  L  S  E  S  H  R  I  F  S  S  G  L
TTACTGACTGAAAGCGCGAAGAGTCTGTCGGAGAGCCACAGGATCTTCTCTTCCGGCCTT    900

 E  E  V  D  I  R  C  L  D  G  N  A  G  V  F  C  W  M  D  L
GAGGAAGTCGACATCCGCTGCTTGGACGGCAATGCCGGGGTCTTCTGCTGGATGGACCTA    960

 R  H  L  L  K  E  A  T  E  D  G  E  L  E  L  W  R  V  I  V
CGGCACCTCCTCAAAGAAGCCACCGAAGACGGCGAGCTCGAGCTGTGGCGCGTGATAGTG   1020

 N  N  V  K  L  N  V  S  P  G  S  S  F  Y  C  A  E  P  G  W
AACAATGTCAAGCTCAATGTGTCCCCCGGTTCGTCGTTTTATTGCGCCGAGCCAGGTTGG   1080
```

FIG. 2

```
Q  M  G  L  A  E  N  Q  L  C  F  N  L  I  H  E  W  P  L  K
CAGATGGGCCTTGCTGAGAATCAGCTTTGCTTTAATTTAATTCACGAGTGGCCGCTGAAA    60

N  P  E  A  S  I  C  T  T  Q  G  A  A  E  F  R  D  I  A  I
AACCCAGAAGCCTCCATTTGTACAACACAAGGAGCAGCTGAATTCAGAGATATAGCTATC   120

F  Q  D  Y  H  G  L  A  E  F  R  E  A  V  A  K  F  M  G  K
TTTCAAGATTATCATGGCTTGGCTGAATTCAGAGAGGCTGTTGCAAAGTTTATGGGGAAA   180

V  R  R  N  R  A  S  F  D  P  D  R  I  V  M  S  G  G  A  T
GTGAGAAGAAACAGAGCTTCATTTGACCCTGATCGGATTGTTATGAGTGGAGGAGCAACT   240

G  A  H  E  M  I  G  F  C  L  A  D  P  G  D  A  F  L  V  P
GGAGCTCATGAAATGATTGGTTTCTGTTTGGCTGATCCTGGCGATGCATTCTTGGTTCCA   300

T  P  Y  Y  P  G  F  D  R  D  L  R  W  R  T  G  V  K  L  I
ACTCCTTATTATCCAGGGTTTGATAGAGATTTGAGATGGAGAACGGGAGTCAAACTCATT   360

P  V  V  C  E  S  S  N  D  Y  Q  I  T  I  E  A  L  E  A  A
CCAGTTGTCTGTGAAAGCTCAAACGATTACCAGATCACCATAGAAGCCCTGGAAGCTGCT   420

Y  E  T  A  Q  E  A  D  I  K  V  K  G  L  V  I  T  N  P  S
TATGAAACCGCACAAGAAGCTGACATCAAGGTAAAGGGTTTGGTCATAACCAACCCATCA   480

N  P  L  G  T  I  I  T  K  D  T  L  E  A  L  V  T  F  T  N
AACCCACTGGGAACAATTATTACCAAGGACACATTAGAAGCTCTAGTCACCTTCACCAAC   540
```

FIG. 2 cont'd

```
 H  K  N  I  H  L  V  C  D  E  I  Y  A  G  Y  R  L  Q  P  R
CACAAGAACATTCATCTGGTGTGTGATGAGATATATGCTGGTTACCGTCTTCAGCCCAGG   600

 A  E  F  T  S  I  A  E  I  I  E  E  D  K  I  C  C  N  R  D
GCCGAATTCACCAGCATAGCCGAGATAATTGAAGAAGATAAAATTTGTTGCAATCGTGAT   660

 L  I  H  I  I  Y  S  L  S  K  D  M  G  F  P  G  F  R  V  G
CTCATCCACATCATTTACAGTTTATCCAAAGACATGGGATTCCCTGGATTTAGAGTTGGC   720

 I  V  Y  S  Y  N  D  A  V  V  S  C  A  R  K  M  S  S  F  G
ATTGTGTATTCATACAATGATGCAGTGGTGAGTTGTGCTCGTAAGATGTCGAGCTTCGGC   780

 L  V  S  S  Q  T  Q  Y  L  I  A  S  M  L  A  D  D  E  F  V
CTAGTATCTTCGCAAACCCAGTATCTGATTGCATCCATGTTAGCAGACGATGAATTTGTA   840

 D  K  F  I  V  E  S  R  K  R  L  A  M  R  H  S  F  F  T  Q
GACAAATTTATTGTAGAGAGCAGAAAGAGGCTGGCAATGAGACATAGTTTTTCACACAA   900

 R  L  A  Q  V  G  I  N  C  L  K  S  N  A  G  L  F  V  W  M
AGACTTGCTCAAGTAGGCATTAACTGTTTAAAAAGCAATGCTGGTCTTTTTGTGTGGATG   960

 D  L  R  R  L  L  K  E  Q  T  F  E  A  E  M  V  L  W  R  V
GATTTGCGTAGACTGCTGAAAGAACAGACATTTGAAGCAGAAATGGTGTTATGGAGAGTA  1020

 I  I  N  E  M  K  L  N  V  S  P  G  S  S  F  H  C  S  E  P
ATTATAAACGAAATGAAACTCAATGTATCTCCTGGTTCGTCTTTCCACTGCTCAGAACCT  1080

 G  W  F  S  V  C  F  A
GGCTGGTTCAGCGTCTGCTTCGCT     1104
```

FIG. 3

```
 Q  M  G  F  A  E  N  Q  L  C  F  D  L  I  E  K  W  V  K  K
CAGATGGGTTTTGCTGAAAATCAGCTTTGCTTTGATTTGATCGAGAAGTGGGTTAAAAAG    60

 N  P  N  A  S  I  C  T  A  E  G  V  E  N  F  K  H  I  A  N
AATCCCAATGCTTCCATCTGCACAGCTGAAGGGGTTGAAAACTTCAAGCACATAGCCAAC   120

 F  Q  D  Y  H  G  L  K  E  F  R  Q  E  V  A  K  L  M  G  K
TTCCAAGACTATCATGGCCTGAAAGAATTTAGACAGGAAGTTGCCAAGTTAATGGGGAAG   180

 A  R  G  G  R  V  T  F  D  P  E  R  I  V  M  S  G  G  A  T
GCAAGAGGCGGCAGAGTGACGTTCGACCCAGAGCGTATTGTGATGAGCGGGGGAGCGACA   240

 G  A  S  E  T  I  M  F  C  L  A  D  P  G  D  A  L  L  V  P
GGCGCCAGCGAGACGATTATGTTTTGCTTGGCGGATCCAGGCGATGCTCTTCTGGTTCCC   300

 T  P  Y  Y  P  G  F  N  R  D  L  R  W  R  T  G  V  Q  I  I
ACTCCTTACTATCCTGGATTCAATAGGGACCTGAGATGGCGAACCGGCGTCCAGATTATT   360

 P  V  Q  C  S  S  S  H  N  F  T  V  T  R  E  A  V  E  A  A
CCCGTGCAATGCAGCAGCTCACACAATTTTACAGTAACACGGGAAGCCGTAGAGGCTGCG   420

 Y  Q  K  A  Q  E  A  N  I  N  V  T  G  L  I  I  T  N  P  S
TACCAGAAAGCTCAAGAAGCCAACATCAATGTCACAGGCTTGATCATCACCAACCCCTCG   480

 N  P  L  G  T  T  L  D  S  Q  T  L  Q  S  L  V  I  F  V  N
AATCCGCTAGGCACCACCTTAGACTCACAAACACTCCAGAGCTTGGTCATCTTCGTCAAC   540
```

FIG. 3 cont'd

```
 D  K  T  I  H  L  V  C  D  E  I  Y  A  A  T  V  F  S  S  P
GACAAGACCATCCACCTGGTCTGCGACGAAATCTATGCCGCCACCGTCTTCAGCTCCCCG   600

 E  F  V  S  I  G  E  I  I  Q  E  M  D  V  N  R  D  L  I  H
GAGTTCGTCAGCATCGGGGAGATCATCCAAGAAATGGACGTCAACCGCGACCTTATCCAC   660

 I  I  Y  S  L  S  K  D  M  G  L  P  G  F  R  V  G  I  V  Y
ATCATCTACAGCTTGTCCAAAGATATGGGTCTCCCCGGTTTCCGGGTAGGTATTGTGTAT   720

 S  Y  N  D  G  V  L  S  C  G  R  R  M  S  S  F  G  L  V  S
TCCTACAACGACGGTGTATTAAGCTGCGGCCGGCGGATGTCGAGCTTTGGGTTGGTCTCG   780

 S  Q  T  Q  Y  F  L  A  T  L  L  S  D  D  E  F  V  D  Y  F
TCACAGACTCAATATTTCCTGGCGACACTGCTGTCCGACGACGAGTTCGTCGATTACTTC   840

 L  R  E  S  S  K  R  L  A  R  R  H  H  K  L  T  R  G  L  E
CTCCGGGAAAGCTCGAAGAGGCTGGCGAGAAGACACCATAAACTCACCAGAGGGCTGGAG   900

 Q  V  G  I  K  C  L  K  S  N  A  G  L  F  V  W  M  D  L  R
CAAGTGGGGATAAAGTGCTTGAAAAGCAATGCCGGACTTTTTGTGTGGATGGACCTGCGG   960

 R  L  L  E  G  P  T  S  F  D  A  E  M  K  L  W  R  T  I  V
AGGCTCCTGGAAGGTCCAACGTCGTTTGATGCAGAAATGAAGCTGTGGCGGACCATCGTC  1020

 N  D  V  K  L  N  V  S  P  G  S  S  F  H  V  A  E  P  G  W
AACGACGTGAAGCTGAACGTGTCGCCGGGATCTTCGTTCCACGTGGCGGAGCCGGGGTGG  1080

 F  R  V  C  F  A
TTCAGAGTATGTTTCGCT    1098
```

FIG. 4

```
 Q  M  G  L  A  E  N  Q  L  C  F  D  L  I  E  D  W  I  R  K
CAGATGGGCCTTGCCGAGAATCAGCTTTGCTTTGATTTGATCGAAGACTGGATTCGCAAA   60

 N  P  Y  A  S  I  C  T  A  E  G  V  D  E  F  K  E  I  A  N
AATCCCTATGCCTCCATTTGTACTGCTGAAGGAGTTGATGAGTTCAAGGAGATTGCAAAC  120

 F  Q  D  Y  H  G  L  P  E  F  R  K  A  V  A  K  F  M  G  K
TTTCAAGATTATCATGGCTTGCCAGAGTTTAGAAAGGCTGTGGCAAAGTTTATGGGAAAA  180

 V  R  G  G  R  V  T  F  D  P  D  R  I  V  M  G  G  G  V  T
GTGAGAGGTGGAAGAGTAACATTTGATCCAGACCGTATAGTCATGGGCGGTGGAGTTACA  240

 G  A  N  E  Q  I  I  F  C  L  A  D  P  G  D  A  F  L  V  P
GGCGCAAACGAGCAAATCATCTTCTGTTTAGCCGACCCTGGCGATGCTTTTCTTGTTCCC  300

 S  P  Y  Y  P  A  F  D  R  D  L  G  W  R  T  G  G  E  I  V
TCACCTTATTATCCAGCATTTGACCGGGACCTGGGATGGCGCACTGGAGGTGAAATAGTT  360

 P  V  P  C  D  S  S  T  N  F  Q  I  T  R  D  A  L  E  E  A
CCTGTTCCCTGTGACAGCTCAACCAATTTCCAGATAACCAGAGATGCATTGGAAGAAGCA  420

 Y  E  K  A  R  E  A  N  I  N  I  K  G  L  I  I  T  N  P  S
TATGAAAAAGCTCGAGAAGCCAACATTAATATTAAAGGCTTGATCATAACAAACCCTTCA  480

 N  P  L  G  I  T  L  D  R  D  T  L  K  S  L  V  S  F  I  D
AACCCACTTGGCATCACCCTAGACAGAGATACTCTTAAAAGCCTAGTGAGCTTCATCGAT  540
```

FIG. 4 cont'd

```
 E  K  N  I  H  F  V  C  D  E  I  Y  A  A  T  L  F  C  P  P
GAAAAGAACATTCACTTTGTCTGCGATGAAATCTATGCTGCCACTCTCTTCTGTCCACCC     600

 K  F  V  S  V  A  E  V  I  Q  E  M  D  C  N  L  D  L  I  H
AAGTTCGTAAGCGTCGCTGAAGTGATCCAAGAAATGGACTGTAATCTTGATCTCATCCAC     660

 I  V  Y  S  L  S  K  D  M  G  L  P  G  F  R  V  G  I  V  Y
ATTGTTTACAGTTTGTCTAAGGACATGGGCCTCCCTGGCTTTAGGGTTGGCATTGTTTAT     720

 S  Y  N  D  A  V  V  S  C  I  R  K  M  S  S  F  G  L  V  S
TCTTATAATGATGCAGTTGTGAGTTGTATCCGCAAGATGTCAAGCTTCGGTTTGGTATCC     780

 S  Q  T  Q  Y  L  L  A  S  M  L  S  D  D  E  F  V  E  K  F
TCACAAACTCAATATTTACTCGCTTCAATGCTTTCTGATGATGAATTTGTGGAAAAGTTT     840

 L  A  E  S  S  K  R  L  A  K  R  Y  H  I  F  T  K  R  L  E
CTAGCGGAAAGCTCAAAGAGGCTGGCAAAAAGGTACCATATTTTCACAAAGAGACTTGAG     900

 K  V  G  I  N  C  L  K  G  N  A  G  L  F  F  W  M  D  L  R
AAAGTGGGGATTAACTGCTTGAAGGGAAATGCAGGTCTTTTCTTCTGGATGGATTTGCGA     960

 H  L  L  Q  Q  E  T  V  D  A  E  M  K  L  W  G  T  I  L  N
CACCTCCTTCAACAAGAAACAGTTGATGCCGAAATGAAGCTATGGGGCACGATTTTGAAC    1020

 D  V  K  L  N  V  S  P  G  S  S  F  H  C  Q  E  P  G  W  F
GATGTGAAACTTAACGTTTCACCAGGCTCTTCCTTTCATTGCCAGGAGCCTGGTTGGTTC    1080

 R  V  C  F  A
AGAGTCTGCTTCGCTG     1096
```

FIG. 5

```
 Q  M  G  F  G  E  N  L  L  C  F  D  L  V  Q  E  W  V  L  S
CAGATGGGATTTGGGGAAAATCTGCTTTGCTTTGATTTAGTTCAAGAATGGGTCTTAAGC    60

 N  P  E  A  S  I  C  T  A  E  G  I  S  D  F  R  D  I  A  I
AACCCAGAAGCCTCTATCTGCACTGCCGAAGGTATAAGTGATTTCAGAGATATCGCTATC   120

 F  Q  D  Y  H  G  L  P  E  F  R  N  A  V  A  N  F  M  A  R
TTTCAGGATTATCACGGCTTGCCAGAGTTCAGAAATGCTGTTGCAAATTTTATGGCAAGA   180

 V  R  G  N  R  V  K  Y  D  P  D  R  I  V  M  S  G  G  A  T
GTGAGAGGGAATAGAGTCAAATACGACCCTGATCGAATTGTTATGAGCGGTGGAGCAACC   240

 G  A  H  E  T  V  A  F  C  L  A  D  P  G  E  A  F  L  G  A
GGAGCACATGAGACGGTTGCCTTTTGTTTGGCTGATCCCGGTGAAGCATTTTTGGGTGCC   300

 T  P  Y  Y  P  G  F  G  R  D  L  R  W  R  T  G  V  Q  L  F
ACTCCTTACTATCCAGGATTTGGTCGAGATTTGAGATGGAGAACAGGAGTTCAACTTTTT   360

 P  V  V  C  D  S  S  N  N  F  K  I  T  R  E  A  V  E  A  A
CCAGTTGTGTGTGACAGTTCTAACAATTTCAAGATTACAAGAGAAGCCGTGGAAGCAGCA   420

 Y  E  K  A  Q  E  D  H  I  R  I  K  G  L  V  L  T  N  P  S
TATGAAAAAGCTCAAGAAGACCACATCAGAATCAAGGGTTTGGTCCTCACAAATCCATCG   480

 N  P  L  G  T  C  L  D  R  E  T  L  R  S  L  V  S  F  I  N
AACCCGCTGGGGACTTGTTTGGACAGAGAAACACTAAGAAGTTTAGTAAGCTTCATTAAT   540
```

FIG. 5 cont'd

```
 E  K  N  I  H  L  V  C  D  E  I  Y  A  A  T  I  F  M  G  Q
GAAAAGAACATCCACTTAGTCTGCGACGAGATTTATGCTGCCACAATCTTCATGGGCCAG     600

 P  D  F  I  S  I  S  E  I  I  E  E  D  I  H  C  N  R  N  L
CCCGATTTCATTAGCATCTCTGAAATTATAGAAGAAGATATTCACTGCAATCGCAATCTC     660

 I  H  L  V  Y  S  L  S  K  D  L  G  F  P  G  F  R  V  G  I
ATCCACCTTGTTTACAGTCTTTCAAAGGATCTGGGGTTCCCAGGCTTTAGGGTCGGCATT     720

 I  Y  S  Y  N  D  T  V  V  S  C  A  C  K  M  S  S  F  G  L
ATATACTCATACAACGATACAGTTGTGAGTTGCGCCTGCAAAATGTCAAGCTTTGGACTT     780

 V  S  S  Q  T  Q  H  L  I  A  S  M  L  S  D  D  E  F  V  D
GTATCATCACAAACTCAACATTTAATCGCTTCAATGTTATCAGATGATGAATTTGTGGAT     840

 R  F  I  T  E  S  A  K  R  L  A  K  R  H  R  A  F  T  W  G
AGGTTCATTACTGAGAGTGCTAAAAGGCTTGCAAAAAGGCACAGAGCCTTCACATGGGGG     900

 L  S  Q  V  G  I  G  C  L  K  S  N  A  G  L  F  F  W  M  D
CTATCTCAAGTAGGCATTGGTTGTTTGAAGAGCAATGCGGGGCTATTTTTCTGGATGGAT     960

 L  H  H  L  L  K  E  Q  T  D  E  A  E  I  E  L  W  K  V  I
TTGCATCATCTCCTCAAGGAGCAAACTGATGAAGCAGAGATAGAACTGTGGAAAGTGATA    1020

 I  N  E  V  K  L  N  V  S  P  G  S  S  F  H  C  A  N  P  G
ATCAACGAAGTTAAATTAAATGTTTCTCCGGGTTCTTCCTTTCATTGCGCTAATCCAGGA    1080

 W  F  R  V  C  F  A  N  M  D  E
TGGTTTCGGGTTTGTTTCGCCAACATGGACGAA    1113
```

ACC SYNTHASE GENE

This application is a continuation of U.S. application Ser. No. 09/043,627 filed Mar. 20, 1998, now U.S. Pat. No. 6,124,525, which was a 35 USC §371 application of PCT/AU96/00591, filed Sep. 20, 1996 and amended under PCT Article 34 on Jun. 10, 1997.

FIELD OF THE INVENTION

This invention relates to ACC synthase and, in particular, novel nucleotide sequences encoding ACC synthase enzymes derived from pineapple, papaya and mango.

BACKGROUND OF THE INVENTION

Ethylene is a well-established plant hormone. It plays an important role in virtually every phase of plant development including seed germination, fruit ripening, leaf and flower senescence, and abscission. The production of ethylene may also be induced by external factors such as mechanical wounding, anaerobiosis, auxin treatment, ultraviolet light, temperature extremes, water stress, and ions such as cadmium, and lithium ions (Abeles, F. B., 1973, Ethylene in Plant Biology, 197–219, Academic Press, London; Yang & Hoffman, 1984, Annu. Rev. Plant Physiol., 35, 155–189).

The pathway for ethylene biosynthesis has been established, the first step of which involves the formation of S-adenosyl-L-methionine (AdoMet) by S-adenosyl-L-methionine synthetase. AdoMet is subsequently converted by S-adenosyl-L-methionine methylthio-adenosine-lyase (ACC synthase; EC 4.4.1.14) to the nonprotein amino acid 1-aminocyclopropane-1 carboxylic acid (ACC), the immediate precursor of ethylene in higher plants (Adams & Yang, 1979, Proc. Natl. Acad. Sci. USA, 76, 170–174). Physiological analysis has suggested that this is the key regulatory step in the pathway, (Kende, 1989, Plant Physiol., 91, 1–4). Thus, the rate of endogenous expression of ACC synthase is considered to limit substantially the rate of ethylene production.

It appears that ACC synthase is encoded by a highly divergent multigene family (for a review, see Theologis, A. 1992, Cell, 70, 181–184; Kende, H., 1993, Annu. Rev. Plant Physiol. Plant Mol. Biol., 44, 283–307). In tomato, for example, ACC synthase is encoded by at least six genes, two of which are expressed in fruit ripening (Van der Straeten et al., 1990, Proc. Natl. Acad. Sci. USA, 87, 4859–4863; Olson et al., 1991, Proc. Natl. Acad. Sci. USA, 88, 5340–5344; Rottmann et al., 1991, J. Mol. Biol., 222, 937–961; Yipp et al., 1992, Proc. Natl. Acad. Sci. USA, 89, 2475–2479).

In addition, reference may be made to an article by Theologis, A. (1992, supra) in which the structure and expression of 20 ACC synthase genes were compared from a variety of plant species including winter squash, zucchini, tomato, Arabidopsis, apple, rice, mung bean and carnation. This comparison suggested that the extensive polymorphism and distinct regulatory networks governing the expression of ACC synthase subfamilies arose early in plant evolution, prior to the divergence of monocotyledons and dicotyledons.

It is well known that endogenous ethylene is often deleterious to crops. In particular, increased ethylene production due to trauma caused by mechanical wounding of fruits and vegetables, and the cutting of flowers greatly diminishes their post harvest quality and storage life. Thus, it has been a major goal of postharvest physiologists to effect suppression of fruit ripening and flower fading by inhibiting the biosynthesis of ethylene.

To this end, a strategy has been developed that takes advantage of the modulation properties of ACC synthase in the control of ethylene biosynthesis. In this regard, reference may be made to International Application Publication No. WO 92/04456 which is directed to inhibition of expression of endogenous ACC synthase using an antisense expression system. This system comprises a DNA molecule capable of generating, when contained in a plant host cell, a complementary RNA that is sufficiently complementary to an RNA transcribed from an endogenous ACC synthase gene to prevent the synthesis of endogenous ACC synthase. Ethylene production in fruits of transgenic tomato plants engineered using this system was inhibited by 99.5% and, as a consequence, fruit ripening was suppressed. In addition, the application of ethylene or propylene to the fruits of these plants restored normal ripening.

Thus, ACC synthase genes may be used as targets for the generation of transgenic plants in which endogenous expression of ACC synthase is inhibited to effect suppression of ethylene production and a concomitant delay in fruit ripening.

The efficacy of this system, however, is predicated on the condition that the antisense RNA is sufficiently complementary to the transcript expressed from the target gene. Accordingly, if there is diversity between different ACC synthase genes, the use in this system for example, of a particular ACC synthase gene from one plant species would not be expected to inhibit the expression of an ACC synthase gene from another plant species. This is supported on page 5 of WO 92/04456 which states: “While the various ACC synthases are generally active in a variety of plant tissues, the DNAs are not completely homologous, and therefore the use of the genetic materials for control of synthesis, for example, using an antisense strategy, does not translate cross species.”

SUMMARY OF THE INVENTION

It is therefore an object of the invention to provide new nucleotide sequences encoding ACC synthase enzymes which have utility as targets for the generation of transgenic plants in which the expression of ACC synthase is substantially controlled to effect the regulation of plant development, and in particular, fruit ripening.

Accordingly, in one aspect of the invention, there is provided a nucleotide sequence encoding an ACC synthase enzyme of pineapple comprising the sequence of nucleotides as shown in FIG. 1.

In another aspect of the invention, there is provided a nucleotide sequence encoding a first ACC synthase enzyme of papaya comprising the sequence of nucleotides as shown in FIG. 2.

In yet another aspect of the invention, there is provided a nucleotide sequence encoding a second ACC synthase enzyme of papaya comprising the sequence of nucleotides as shown in FIG. 3.

In still yet another aspect of the invention, there is provided a nucleotide sequence encoding a first ACC synthase enzyme of mango comprising the sequence of nucleotides as shown in FIG. 4.

In a further aspect of the invention, there is provided a nucleotide sequence encoding a second ACC synthase enzyme of mango comprising the sequence of nucleotides as shown in FIG. 5.

The term “nucleotide sequence” as used herein designates mRNA, RNA, cRNA, cDNA or DNA.

The invention also provides homologs of the nucleotide sequences of the invention described in FIGS. 1–5. Such "homologs", as used in this specification include all nucleotide sequences encoding sub-sequences of the nucleotide sequences according to FIGS. 1–5.

The homologs of the invention further comprise nucleotide sequences that hybridize with any one of the nucleotide sequences of the invention under stringent conditions. Suitable hybridization conditions are discussed below.

The homologs of the invention may be prepared according to the following procedure:

(i) designing primers which are preferably degenerate which span at least a fragment of a nucleotide sequence of the invention; and (ii) using such primers to amplify, via PCR techniques, said at least a fragment from a nucleic acid extract obtained from a suitable host. In this regard, the suitable host is preferably a fruit, fruit part or cell thereof obtained from a pineapple plant, a mango plant or a papaya plant.

BRIEF DESCRIPTION OF THE DRAWINGS

In order that the invention may be readily understood and put into practical effect, particular preferred embodiments will now be described by way of example with reference to the following figures in which:

FIG. 1 (SEQ ID NOS:1 and 2 respectively) shows the nucleotide and deduced amino acid sequences encoding an ACC synthase enzyme of pineapple;

FIG. 2 (SEQ ID NOS:3 and 4 respectively) shows the nucleotide and deduced amino acid sequences encoding a first ACC synthase enzyme of papaya;

FIG. 3 (SEQ ID NOS:5 and 6 respectively) shows the nucleotide and deduced amino acid sequences encoding a second ACC synthase enzyme of papaya;

FIG. 4 (SEQ ID NOS:7 and 8 respectively) shows the nucleotide and deduced amino acid sequences encoding a first ACC synthase enzyme of mango; and FIG. 5 (SEQ ID NOS:9 and 10 respectively) shows the nucleotide and deduced amino acid sequences encoding a second ACC synthase enzyme of mango.

DETAILED DESCRIPTION OF THE INVENTION

"Hybridization" is used here to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA, U pairs with A and C pairs with G.

Typically, nucleotide sequences to be compared by means of hybridization are analyzed using dot blotting, slot blotting, or Southern blotting. Southern blotting is used to determine the complementarity of DNA sequences. Northern blotting determines complementarity of DNA and RNA sequences. Dot and Slot blotting can be used to analyze DNA/DNA or DNA/RNA complementarity. These techniques are well known by those of skill in the art. Typical procedures are described in CURRENT PROTOCOLS IN MOLECULAR BIOLOGY (Ausubel, et al., eds.) (John Wiley & Sons, Inc. 1995) at pages 2.9.1 through 2.9.20. Briefly, for Southern blotting, DNA samples are separated by size using gel electrophoresis. The size-separated DNA samples are transferred to and immobilized on a membrane (typically, nitrocellulose) and the DNA samples are probed with a radioactive, complementary nucleic acid. In dot blotting, DNA samples are directly spotted onto a membrane (nitrocellulose or nylon). In slot blotting, the spotted DNA samples are elongated. The membrane is then probed with a radioactive complementary nucleic acid.

A probe is a biochemical labeled with a radioactive isotope or tagged in other ways for ease in identification. A probe is used to identify a gene, a gene product or a protein. Thus a nucleotide sequence probe can be used to identify complementary nucleotide sequences. An mRNA probe will hybridize with its corresponding DNA gene.

Typically, the following general procedure can be used to determine hybridization under stringent conditions. A nucleotide sequence according to the invention (such as those shown in FIGS. 1–5 or a sub-sequence thereof) will be immobilized on a membrane using one of the above-described procedures for blotting. A sample nucleotide sequence will be labeled and used as a "probe." Using procedures well known to those skilled in the art for blotting described above, the ability of the probe to hybridize with a nucleotide sequence according to the invention can be analyzed.

One of skill in the art will recognize that various factors can influence the amount and detectability of the probe bound to the immobilized DNA. The specific activity of the probe must be sufficiently high to permit detection. Typically, a specific activity of at least $10^8$ dpm/$\mu$g is necessary to avoid weak or undetectable hybridization signals when using a radioactive hybridization probe. A probe with a specific activity of $10^8$ to $10^9$ dpm/$\mu$g can detect approximately 0.5 pg of DNA. It is well known in the art that sufficient DNA must be immobilized on the membrane to permit detection. It is desirable to have excess immobilized DNA and spotting 10 $\mu$g of DNA is generally an acceptable amount that will permit optimum detection in most circumstances. Adding an inert polymer such as 10% (w/v) dextran sulfate (mol. wt. 500,000) or PEG 6000 to the hybridization solution can also increase the sensitivity of the hybridization. Adding these polymers has been known to increase the hybridization signal. See Ausubel, supra, at p 2.10.10.

To achieve meaningful results from hybridization between a first nucleotide sequence immobilized on a membrane and a second nucleotide sequence to be used as a hybridization probe, (1) sufficient probe must bind to the immobilized DNA to produce a detectable signal (sensitivity) and (2) following the washing procedure, the probe must be attached only to those immobilized sequences with the desired degree of complementarity to the probe sequence (specificity).

"Stringency," as used in this specification, means the condition with regard to temperature, ionic strength and the presence of certain organic solvents, under which nucleic acid hybridizations are carried out. The higher the stringency used, the higher degree of complementarity between the probe and the immobilized DNA.

"Stringent conditions" designates those conditions under which only nucleotide sequences that have a high frequency of complementary base sequences will hybridize with each other.

Exemplary stringent conditions are (1) 0.75 M dibasic sodium phosphate/0.5 M monobasic sodium phosphate/1 mM disodium EDTA/1% sarkosyl at about 42° C. for at least about 30 minutes, (2) 6.0 M urea/0.4% sodium lauryl sulfate/0.1% SSC at about 42° C. for at least about 30 minutes, (3) 0.1×SSC/0.1% SDS at about 68° C. for at least about 20 minutes, (4) 1×SSC/0.1% SDS at about 55° C. for about one hour, (5) 1×SSC/0.1% SDS at about 62° C. for about one hour, (6) 1×SSC/0.1% SDS at about 68° C. for about one hour, (7) 0.2×SSC/0.1% SDS at about 55° C. for about one hour, (8) 0.2×SSC/0.1% SDS at about 62° C. for about one hour, and (9) 0.2×SSC/0.1% SDS at about 68° C. for about one hour. See, e.g. CURRENT PROTOCOLS IN MOLECULAR BIOLOGY (Ausubel, et al., eds.) (John Wiley & Sons, Inc. 1995), pages 2.10.1–2.10.16 of which are hereby incorporated by reference and Sambrook, et al., MOLECULAR CLONING. A LABORATORY MANUAL (Cold Spring Harbor Press, 1989) at §§1.101–1.104.

Stringent washes are typically carried out for a total of about 20 minutes to about 60 minutes. In certain instances, more than one stringent wash will be required to remove sequences that are not highly similar to the nucleotide sequences shown in FIGS. 1–5 or a sub-sequence thereof. One of skill in the art will appreciate that other longer or shorter times may be employed for stringent washes to ensure identification of sequences similar to the nucleotide sequences designated in FIGS. 1–5.

While stringent washes are typically carried out at temperatures from about 42° C. to about 68° C., one of skill in the art will appreciate that other temperatures may be suitable for stringent conditions. Maximum hybridization typically occurs at about 20 to about 25° C. below the $T_m$ for DNA-DNA hybrids. It is well known in the art that $T_m$ is the melting temperature, or temperature at which two nucleotide sequences dissociate. Methods for estimating $T_m$ are well known in the art. See, e.g. Ausubel, supra, at page 2.10.8. Maximum hybridization typically occurs at about 10 to about 15° C. below the $T_m$ for DNA-RNA hybrids.

Other typical stringent conditions are well-known in the art. One of skill in the art will recognize that various factors can be manipulated to optimize the specificity of the hybridization. Optimization of the stringency of the final washes can serve to ensure a high degree of hybridization between the nucleotide sequences shown in FIGS. 1–5 (or subsequence thereof) and other similar nucleotide sequences.

In a typical hybridization procedure, DNA is first immobilized on a membrane such as a nitrocellulose membrane or a nylon membrane. Procedures for DNA immobilization on such membranes are well known in the art. See, e.g., Ausubel, supra at pages 2.9.1–2.9.20. The membrane is prehybridized at 42° C. for 30–60 minutes in 0.75 M dibasic sodium phosphate/0.5 M monobasic sodium phosphate/1 mM disodium EDTA/1% sarkosyl. Membranes are then hybridized at 42° C. in ACES hybridization solution (Life Technologies, Inc., Gaithersburg, Md.) containing labeled probe for one hour. Next, membranes are subjected to two high stringency 10 minute washes at 42° C. in 0.75 M dibasic sodium phosphate/0.5 M monobasic sodium phosphate/1 mM disodium EDTA/1% sarkosyl. Following this, the membranes are washed with 2×SSC at room temperature, to remove unbound probe.

In another typical hybridization procedure, DNA immobilized on a membrane is hybridized overnight at 42° C. in prehybridization solution. Following hybridization, blots are washed with two stringent washes, such as 6.0 M urea/0.4% sodium lauryl sulfate/0.1% SSC at 42° C. Following this, the membranes are washed with 2×SSC at room temperature.

Autoradiographic techniques for detecting radioactively labeled probes bound to membranes are well known in the art.

This invention further includes within its scope homologs which comprise synonymous DNA sequences that code for the ACC synthase enzymes or portions thereof shown in FIGS. 1–5.

In another aspect, the invention resides in a method of isolating at least a fragment of an ACC synthase gene involved in regulation of fruit ripening, said method including the steps of:

(a) lysing ripened tissue of a fruit to produce a lysate;

(b) separating protein and carbohydrates from the lysate to produce an extract comprising substantially intact RNA wherein said extract is substantially incapable of inhibiting cDNA synthesis;

(c) reverse transcribing the RNA of said extract with an antisense primer complementary to a portion of said ACC synthase gene to synthesize a cDNA; and (d) subjecting the cDNA to PCR with a sense primer and an antisense primer which are complementary to different portions of said ACC synthase gene to amplify said at least a fragment of said ACC synthase gene.

Preferably, the fruit is pineapple, = or mango.

Suitably, the step of lysing (step a)) is effected by lysing the ripened tissue in a medium comprising 150 mM Tris pH 7.5 with boric acid, 2% SDS, 50 mM EDTA, 1% mercaptoethanol. Preferably, 2–3 volumes of this medium is used per volume of ripened tissue.

Preferably, the step of separating (step (b)) is effected by at least one chloroform-isoamyl alcohol extraction of the lysate followed by at least two phenol-chloroform extractions of an aqueous phase resulting from the at least one chloroform-isoamyl alcohol extraction. Alternatively, the step of separating may be effected by at least one chloroform-isoamyl alcohol extraction of the lysate followed by at least two phenol-chloroform-isoamyl alcohol extractions of an aqueous phase resulting from the at least one chloroform-isoamyl alcohol extraction.

The primers used for reverse transcription (step (c)) and PCR (step (d)) are preferably degenerate primers. Suitably, the degenerate primers correspond to conserved portions of different ACC synthase isoforms. Preferably, the degenerate primers are selected from the group consisting of: 5'TA(C/T)TT(C/T)GA(C/T)GG(A/C/G/T)TGGAA(A/G)GC 3' (SEQ ID NO:11); 5'TC(A/G)TCCAT(A/G)TT(A/C/G/T)GC(A/G)AA(A/G)CA 3' (SEQ ID NO:12); 5' CA(A/G)ATGGG(A/C/G/T)(C/T)T(A/C/G/T)GC(A/C/G/T)GA(A/G)AA 3'(SEQ ID NO:13); 5'AC(A/C/G/T)C(G/T)(A/G)AACCA(A/C/G/T)CC(A/C/G/T)GG(C/T)TC 3'(SEQ ID NO:15); 5' GCTCTAGATA(C/T)TT(C/T)GA(C/T)GG(A/C/G/T)TGGAA(A/G)GC 3' (SEQ ID NO:16); 5'GCGAATTC(A/G)TCCAT(A/G)TT(A/C/G/T)GC(A/G)AA(A/G)CA3' (SEQ ID NO:17);5' CCTGATCA(A/G)ATGGG(A/C/G/T)(C/T)T(A/C/G/T)GC(A/C/G/T)GA(A/G)AA 3' (SEQ ID NO:18); and 5' CTCTGCAGC(A/G)AA(A/G)CA(A//C/G/T)AC(A/C/G/T)C(G/T)(A/G)AACCA 3' (SEQ ID NO:19).

Preferably, when the fruit is pineapple, the antisense primer for reverse transcription is 5' TC(A/G)TCCAT(A/G)TT(A/C/G/T)GC(A/G) AA(A/G)CA 3' (SEQ ID NO:12), the sense primer for PCR is 5' TA(C/T)TT(C/T) GA(C/T)GG(A/C/G/T)TGGAA(A/G)GC 3'(SEQ ID NO:11) OR 5' CA(A/G)ATGGG(A/C/G/T)(C/T)T(A/C/G/T)GC(A/C/G/T)GA(A/G)AA3'(SEQ ID NO:13), and the antisense primer for PCR is 5' TC(A/G)TCCAT(A/G)TT(A/C/G/T)GC(A/G)AA(A/G)CA 3' (SEQ ID NO:12) or 5' AC (A/C/G/T)C(G/T)(A/G)AACCA(A/C/G/T)CC(A/C/G/T)GG(C/T)TC 3' (SEQ ID NO:15).

Suitably, when the fruit is mango or papaya, the antisense primer for reverse transcription is 5' GCGAATTCC(A/G)TCCAT(A/G)TT (A/C/G/T)GC(A/G)AA(A/G)CA (SEQ ID NO:17) 3', the sense primer for PCR is 5' GCTCTAGATA(C/T)TT(C/T)GA(C/T)GG(A/C/G/T)GG(A/C/G/T)TGGAA(A/G)GC 3'(SEQ ID NO:16) or 5' CCTGATCA(A/G)ATGGG(A/C/G/T) (C/T)T(A/C/G/T)GC(A/C/G/T)GA(A/G)AA 3'(SEQ ID NO:18), and the antisense primer for PCR is 5' GCGAATTC(A/G) TCCAT(A/G)TT (A/C/G/T) GC(A/G)AA(A/G)CA 3' (SEQ ID NO:17) or 5' CTCTGCAGC(A/G) AA(A/G)CA(A/C/G/T)AC(A/C/G/T) C(G/T)(A/G)AACCA (SEQ ID NO:19) 3'.

Preferably, in step (d) comprises a first PCR and a second PCR wherein the second PCR employs a nested pair of primers relative to those used in the first PCR.

The DNA sequences of the invention have utility as targets for the generation of transgenic variants of pineapple, papaya and mango in which the expression of ACC synthase is substantially inhibited to effect suppression of fruit senescence.

The method of generating a transgenic pineapple with inhibited fruit senescence includes the steps of introducing into a pineapple plant, or plant part or cell thereof a vector comprising the nucleotide sequence of FIG. 1 wherein said sequence is operably linked, in the sense orientation, to one or more regulatory nucleotide sequences, and growing said plant or plant part or cell thereof to generate the transgenic variety of pineapple.

The invention also comprises a method of generating a transgenic variety of pineapple wherein fruit senescence is substantially inhibited, said method including the steps of introducing into a pineapple plant, or plant part or cell thereof a vector comprising the nucleotide sequence of FIG. 1 wherein said sequence is operably linked, in the antisense orientation, to one or more regulatory nucleotide sequences, and growing said plant or plant part or cell thereof to generate the transgenic variety of pineapple.

The method of generating a transgenic papaya plant with inhibited fruit senescence includes the steps of introducing into a papaya plant, or plant part or cell thereof a vector comprising the nucleotide sequence of FIG. 2 and/or FIG. 3 wherein said sequence is operably linked, in the sense orientation, to one or more regulatory nucleotide sequences, and growing said plant or plant part or cell thereof to generate the transgenic variety of papaya.

The invention further comprises a method of generating a transgenic variety of papaya wherein fruit senescence is substantially inhibited, said method including the steps of introducing into a papaya plant, or plant part or cell thereof a vector comprising the nucleotide sequence of FIG. 2 and/or FIG. 3 wherein said sequence is operably linked, in the antisense orientation, to one or more regulatory nucleotide sequences, and growing said plant or plant part or cell thereof to generate the transgenic variety of papaya.

The method of generating a transgenic mango plant with inhibited fruit senescence includes the steps of introducing into a mango plant, or plant part or cell thereof a vector comprising the nucleotide sequence of FIG. 4 and/or FIG. 5 wherein said sequence is operably linked, in the sense orientation, to one or more regulatory nucleotide sequences, and growing said plant or plant part or cell thereof to generate the transgenic variety of mango.

The invention still further comprises a method of generating a transgenic variety of mango wherein fruit senescence is substantially inhibited, said method including the steps of introducing into a mango plant, or plant part or cell thereof a vector comprising the nucleotide sequence of FIG. 4 and/or FIG. 5 wherein said sequence is operably linked, in the antisense orientation, to one or more regulatory nucleotide sequences, and growing said plant or plant part or cell thereof to generate the transgenic variety of mango.

A vector according to the invention may be a prokaryotic or a eukaryotic expression vector, which are well known to those of skill in the art. Such vectors may contain one or more copies of the nucleotide sequences according to the invention.

Regulatory nucleotide sequences which may be utilized to regulate expression of the nucleotide sequences of FIGS. 1–5 or homologs thereof include, but are not limited to, a promoter, an enhancer, and a transcriptional terminator. Such regulatory sequences are well known to those of skill in the art.

Suitable promoters which may be utilized to induce expression of the nucleotide sequences of the invention include constitutive promoters and inducible promoters. A particularly preferred promoter which may be used to induce such expression is the Cauliflower Mosaic Virus (CaMV) 35S promoter.

Any suitable transcriptional terminator may be used which effects termination of transcription of a nucleotide sequence in accordance with the invention. Preferably, the nopaline synthase (NOS) terminator, as for example disclosed in U.S. Pat. No. 5,034,322, is used as the transcription terminator.

The vector may also include a selection marker such as an antibiotic resistance gene which can be used for selection of suitable transformants. Examples of such resistance genes include the nptII gene which confers resistance to the antibiotics kanamycin and G418 (Geneticin®) and the hph gene which confers resistance to the antibiotic hygromycin B.

The vector may be introduced by a number of methods including transfection, projectile bombardment, electroporation or infection by *Agrobacterium tumefaciens.*

Of course it will be appreciated that the nucleotide sequence which is operably linked to the regulatory nucleotide sequence may be a homolog of the corresponding nucleotide sequence as described above.

With reference to the above methods wherein the nucleotide sequence is expressed in the sense orientation, such methods are predicated on RNA-mediated suppression (also termed gene-silencing or co-suppression) wherein transcription products of the nucleotide sequence which are substantially homologous to corresponding transcripts of an endogenous gene cause inhibition of expression of the endogenous gene. In this regard, reference may be made to WO 90/12084 (which is hereby incorporated by reference) which discloses methods for engineering the transgenic plants based on RNA-mediated suppression.

With reference to the above methods wherein the nucleotide sequence is expressed in the antisense orientation, such methods are based on antisense-mediated suppression as, for example, described in WO 92/04456 (which is hereby incorporated by reference).

It will of course be appreciated that gene transplacement by homologous recombination may also be used to effect the generation of suitable transgenic plants. Such methods are well known to persons of skill in the art.

EXAMPLE 1

Amplification of an ACC Synthase Gene from Pineapple

Experimental Strategy:

A rapid and simple procedure for extracting efficiently intact RNA from pineapple fruit pulp, a tissue rich in polysaccharides and carbohydrates, required the modification and integration of several conventional methods (Logemann et al., 1987, Anal. Biochem., 163, 16–20; Lopez-Gomez and Gomez-Lim, 1992, HortScience, 27, 440–442; Schultz et al., 1994, Plant Mol. Biol., Reporter 12, 310–318; Su and Gibor, 1988, Anal. Biochem., 174, 650–657). The method was optimised such that the RNA isolated from the plant material satisfied three criteria: (1)

RNA should be substantially intact to furnish reproducible migration patterns following gel electrophoresis; (2) the yield of RNA should be sufficient so that relatively small amounts of tissue could be used; (3) the RNA should be free from any contaminants that could interfere with cDNA synthesis or Northern blots.

We developed a method fulfilling all three criteria. The aim was to extract high quality RNA from mature green and ripe pineapple fruit (*Ananas comosus* L.; cultivar; Smooth Cayenne, Queensland clone 30) flesh. The same methodology was also used to extract high molecular weight genomic DNA for southern analysis.

Materials and Methods:

All glassware, utensils and centrifuge tubes were rinsed with water containing 0.1% diethyl pyrocarbonate (DEPC) and autoclaved in order to remove RNA degrading enzymes and protein contamination. Solutions were incubated with DEPC (0.1% final concentration) overnight and autoclaved to denature any RNases present in said solutions.

Nucleic Acid Extraction Procedure for Pineapple

Pineapple fruit tissue (derived from *Ananas comosus* L.) was frozen in liquid nitrogen and stored at −70° C. In a liquid-nitrogen-filled mortar, pineapple fruit tissue (10 g) or pineapple leaf tissue (1–4 g), was ground to a fine powder. While still frozen the fruit powder was transferred to a 100 mL beaker containing 30 mL of lysis buffer (150 mM Tris pH 7.5 with boric acid, 2% SDS, 50 mM EDTA, 1% mercaptoethanol) and stirred for 5 min at room temperature. 0.25 volume of absolute ethanol and 0.11 volume of 5 M potassium acetate were added to the homogenate and stirred for a further 3 min. One volume of chloroform isoamyl alcohol (24:1) (SEVAG) was added subsequently and mixed for an additional 3 min. The homogenate was centrifuged at 18,000 rpm for 10 min in a prechilled (4° C.) centrifuge. The recovered aqueous phase was extracted twice with phenol-chloroform (1:1) or until to interphase (proteins and carbohydrates) was apparent.

After careful removal of the aqueous phase, nucleic acids were precipitated by the addition of 2.25 volumes of absolute ethanol. After incubation for 2 hrs at −20° C., nucleic acids were centrifuged for 30 min at 18,000 rpm, dried and redissolved in 10 mL of DEPC treated $dH_2O$. 8 M LiCl was added to a final concentration of 3 M and the mixture incubated overnight at −20° C. RNA was collected by centrifugation (18,000 rpm, for 30 min at 4° C.) and washed twice in 80% ethanol at room temperature and dried. The RNA pellet was subsequently resuspended in 300 μL of DEPC treated water, and RNA precipitated by adding sodium acetate to a final concentration of 0.3 M and 2.5 volumes of absolute ethanol. After overnight incubation at −70° C., the RNA was pelleted by centrifugation for 30 min at 14,000 rpm (4° C.). The pellet was washed twice in 80% ethanol and vacuum dried for 10 min. The RNA was then resuspended in 50 μL of DEPC treated sterile water, spectrophotometrically quantified and stored at −70° C.

Genomic DNA was pelleted from the supernatant collected after the LiCl precipitation step by the addition of 2 volumes of absolute ethanol, kept at −20° C. for 2 hrs and centrifuged at 12,000 rpm for 30 min. The DNA pellet was resuspended in 500 μL of TE buffer, spectrophotometrically quantified and stored at −20° C.

Formaldehyde Denaturing Gel Electrophoresis of RNA

Ten μg of total RNA was electrophresed on a 1% agarose gel at 80 V for 1 hr. The gel was prepared by adding 0.5 g of agarose, 5 mL of 10× MOPS, 36 mL of DEPC treated water and 9 mL of formaldehyde. RNA samples were prepared by adding 25 μl of RNA loading buffer (containing ethidium bromide) to 5 μL of RNA and denatured at 70° C. for 5 min, followed by chilling on ice for 2 min. Electrophoresis was conducted in 1× MOPS buffer. The gel was photographed immediately after electrophoresis.

DNA Gel Electrophoresis

The integrity of genomic DNA was checked by electrophoresis on a 0.8% agarose gel (prepared in 1× TBE buffer) at 80 volts for 1 hr. 10× loading buffer was added to approximately 4 μg of DNA and electrophoresis conducted in 1× TBE buffer. The gel was stained in an ethidium bromide solution (66 μg/mL) and photographed as described above.

Design of Primers for Amplification of ACC Synthases From Higher Plants

Homology studies of several ACC synthase proteins revealed various conserved regions among this family of proteins. Those regions were used in designing degenerate oligonucleotides by reverse translating the amino acid sequence and taking in account the degeneracy of the genetic code. As a result, several degenerate oligonucleotides were synthesized and are shown in Table 1.

Amplification of acacc1

Reverse transcription of RNA from ripe pineapple tissue was performed by using 1 μg total RNA and 2.5 U of Moloney Murine Leukemia Virus (MMLV) reverse transcriptase in a reaction mixture of 10 mM Tris-HCl, pH 8.3 containing 50 mM KCl, 5 mM $MgCl_2$, 1 mM of each dNTP, 1 U RNase inhibitor and 0.75 μM of oligonucleotide primer EZ-4 (Table 1). The reaction mixture was incubated for 30 min at 42° C. and then heated to 99° C. for 5 min to inactivate the reverse transcriptase. The cDNA produced was amplified with 2.5 U AmpliTaq DNA Polymerase in a reaction mixture of 10 mM Tris-HCl, pH 8.3 containing 2 mM $MgCl_2$, 50 mM KCl, and 0.15 μM of EZ-2 and EZ-4 (Table 1). After an initial 3 min denaturing period at 94° C., the PCR parameters were 1 min template denaturation at 94° C., 1 min primer annealing at 48° C. and 2 min primer extension at 72° C. for 45 cycles. A final extension step of 15 min at 72° C. was used subsequently to ensure full length amplification products.

The products of this PCR reaction were further amplified using a second set of oligonucleotide primers EZ-5 and EZ-7 (Table 1). The reaction consisted of adding to a tube a sample of the products obtained from the previous amplification and 2.5 U AmpliTaq DNA Polymerase in a reaction mixture of 10 mM Tris-HCl, pH 8.3 containing 1.5 mM $MgCl_2$, 50 mM KCl, 0.2 mM of each dNTP, 0.1% gelatin and 0.15 μM of each primer in a total volume of 100 μL. The PCR parameters were 30 sec template denaturation at 94° C., 30 sec primer annealing at 48° C. and 1.5 min primer extension at 72° C. for 30 cycles. The PCR products were analyzed on 0.8% agarose gels and visualized with ethidium bromide.

Subcloning and Sequencing of PCR Products

The cDNA amplified by PCR was ligated into pBluescript ($SK^+$) (Stratagene, La Jolla, Calif.). The ligation mixtures were used to transform *E. coli* DH5α. Transformants were selected on LB plates containing ampicillin (50 mg/ml) and X-gal (0.033% w/v). Plasmid DNA was isolated using the alkaline lysis method.

DNA sequencing was carried out using Applied Biosystems PRISM™ Ready Reaction DyeDeoxy™ Terminator Cycle Sequencing kit.

Results:

After optimising all the parameters for the PCR amplification reactions, a DNA band of approximately 1.1 Kb could be observed in electrophoresis gels. The DNA fragment corresponding to this band was subcloned into pBluescript and named acacc1. The nucleotide sequence of acacc1 and the deduced amino acid sequence thereof are shown in FIG. 1. Comparison of these sequences with other published ACC synthase sequences indicates that acacc1 is a cDNA coding for a member of the ACC synthase family in pineapple. Searches in all the available protein and DNA data banks failed to find 100% homology with any existing clone. The highest homology found at the DNA level using the blastn program was 65% with *Nicotiana tabacum* mRNA clone #X65982 (EMBL data bank). Similarly, at the protein level the highest homology found using the program BLASTX was 65% with soybean sequence entry # S25002 in the PIR database.

Analysis of the acacc1 DNA sequence reveals that it is 1080 bp in size and represents approximately 75% of the coding region.

EXAMPLE 2

Amplification of ACC Synthase Genes from Papaya

Materials and Methods:

Tissue preparation

Using a sharp knife, the papaya fruit (derived from *Carica papaya* L.) was cut in half and the seeds removed. The skin was cut away and the fruit flesh was diced into small cubes which were immediately frozen in liquid nitrogen. The liquid nitrogen was drained off and the tissue was stored at −80° C.

RNA Extraction Procedure for Papaya

Three to six grams of ripe papaya fruit tissue was ground in liquid nitrogen using a pre-cooled mortar and pestle and dissolved in 2 to 3 volumes of extraction buffer (150 mM Tris pH 7.5 with boric acid, 2% SDS, 50 mM EDTA, 1% mercaptoethanol). 0.25 volumes of ethanol, 0.11 volumes of 5 M potassium acetate and 1 volume of SEVAG was added to the mixture before it was centrifuged at 18,000 R.P.M. for 30 min at 4° C. The upper aqueous layer was transferred to a new tube and 3 ×phenol/chloroform/isoamyl alcohol 50/49/1 extractions were performed on it. To the final upper layer, 2.25 volumes of ethanol was added and the solution was incubated at −20° C. for 2 hrs to precipitate all nucleic acids. The solution was subsequently centrifuged at 18,000 rpm for 30 min at 4° C., the pellet washed with 80% ethanol and air dried for 10 min. The pellet was resuspended in 10 mL of DEPC water before the addition of 6 mL of 8 M LiCl. This solution was incubated overnight at −20° C.

The solution was centrifuged at 18,000 rpm for 30 min at 4° C. The RNA pellet was washed with 80% ethanol before being vacuum dried. The pellet was then resuspended in 300 μL of DEPC water and precipitated by adding 2.5 volumes of ethanol, 0.1 volumes of 3 M sodium acetate and incubated at −80° C. for 20 min. The solution was centrifuged at 14,000 rpm for 30 min at 4° C., and the pellet was washed twice with 80% ethanol before it was vacuum dried and resuspended in 50 μL of DEPC water.

Amplification of capacc1 and capacc2

Reverse transcription of RNA from ripe papaya fruit tissue was performed using 1 μg total RNA and 2.5 U of Moloney Murine Leukemia Virus (MMLV) reverse transcriptase in a reaction mixture of 10 mM Tris-HCl, pH 8.3 containing 50 mM KCl, 5 mM $MgCl_2$, 1 mM of each dNTP, 1 U RNase inhibitor and 0.75 μM of oligonucleotide primer OLE-4 (Table 1). The reaction mixture was incubated for 30 min at 42° C. and then heated to 99° C. for 5 min to inactivate the reverse transcriptase. The cDNA produced was amplified with 2.5 U AmpliTaq DNA Polymerase in a reaction mixture of 10 mM Tris-HCl, pH 8.3 containing 2 mM $MgCl_2$, 50 mM KCl, and 0.15 μM of OLE-2 and OLE-4 (Table 1). After an initial 3 min denaturing period at 94° C., the PCR parameters were 1 min template denaturation at 94° C., 1 min primer annealing at 48° C. and 2 min primer extension at 72° C. for 45 cycles. A final extension step of 15 min at 72° c. was used subsequently to ensure full length amplification products.

The products of this PCR reaction were further amplified using a second set of oligonucleotide primers OLE-5 and OLE-6 (Table 1). The reaction consisted of adding to a tube a sample of the products obtained from the previous amplification and 2.5 U AmpliTaq DNA Polymerase in a reaction mixture of 10 mM Tris-HCl, pH 8.3 containing 1.5 mM $MgCl_2$, 50 mM KCl, 0.2 mM of each dNTP, 0.1% gelatin and 0.15 μM of each primer in a total volume of 100 μL. The PCR parameters were 30 sec template denaturation at 94° C., 30 sec primer annealing at 48° C. and 1.5 min primer extension at 72° C. for 30 cycles. The PCR products were analyzed on 0.8% agarose gels and visualized with ethidium bromide.

Results:

After reverse transcription and PCR amplification, a DNA band of approximately 1.1 Kb could be observed in electrophoresis gels. The DNA fragment corresponding to this band was purified from the gel and subcloned into pBluescript. Analysis of several recombinant plasmids revealed the presence of two different inserts of approximately the same length but with different restriction patterns. The two different clones were named capacc1 and capacc2 respectively. The DNA and deduced amino acid sequences corresponding to capacc1 and capacc2 are shown respectively in FIG. 2 and FIG. 3. Comparison of these sequences with other published ACC synthase sequences indicates that capacc1 and capacc2 are cDNAs coding for members of the ACC synthase family in papaya. Searches in all the available protein and DNA data banks failed to find 100% homology with any existing clone. The highest homology found for capacc1 was 74% at the DNA level with a *Pelargonium hortorum* clone (#U17231, GenBank database) and 76% at the protein level with a *Pelargonium hortorum* ACC synthase (#1124858 GenBank database).

For capacc2, the highest homology found at the DNA level was 72% respectively with a *Pelargonium hortorum* mRNA clone (# U17231, GenBank database) and an *Arabidopsis thaliana* mRNA clone (# M95595, GenBank database). At the protein level, the highest homology found for capacc2 was 71% with an ACC synthase from *Arabidopsis thaliana* (entry # 1254990, GenBank database).

Analysis of the capacc1 and capacc2 DNA sequences reveals that the sizes of capacc1 and capacc2 are 1104 bp and 1098 bp respectively. Each of these DNA sequences represents approximately 75% of the coding sequence relating thereto.

EXAMPLE 3

Amplification of ACC Synthase Genes from Mango

MATERIALS AND METHODS

RNA Extraction Procedure for Mango Tissue

Six grams of frozen ripe mango tissue (derived from *Mangifera indica* L.) was ground under liquid nitrogen until it formed a fine powder. The ground tissue was transferred into a falcon tube containing 15 mL extraction buffer (150 mM Tris pH 7.5 with boric acid, 2% SDS, 50 mM EDTA, 1% mercaptoethanol) and vortexed for 2 min. 0.25 vol of ethanol was then added and vortexed for 30 sec. 0.11 vol of 5 M potassium acetate was then added and vortexed for 30 sec. 1 vol SEVAG was then added, vortexed for 1 min and transferred into a DEPC treated centrifuge tube. The tube was centrifuged for 30 min at 18,000 rpm at 4° C. Phenol-SEVAG extractions were performed until no interface layer was observed. The centrifugation steps were performed in falcon tubes for 1 min at 4,500 rpm at 4·C. The supernatant was transferred into a new tube and 2.25 vol of ethanol and the nucleic acids were precipitated at −20° C. for 20 min. The tube was centrifuged for 30 min at 18,000 rpm at 4° C. in a SS34 rotor. The pellet was washed with 80% ethanol and allowed to dry inverted on a tissue and was subsequently resuspended in 10 mL DEPC water and 6 mL LiCl (8 M) was subsequently added and the RNA was precipitated overnight at −20° C.

The tube was subsequently centrifuged for 30 min at 18,000 rpm at 4° C. in a SS34 rotor, the pellet containing the RNA was washed with 80% ethanol and all traces of the ethanol was carefully removed. The pellet was resuspended in 300 μL of DEPC water to which was added 2.5 vol of ethanol and 0.1 vol of 3 M NaAcetate (pH 5.2). The RNA was precipitated at −80° C. for 20 min and the tube was centrifuged in a microfuge at 4° C. for 30 min and the pellet washed with 80% ethanol. The pellet was finally resuspended in 50 μL of DEPC water and stored at −80° C.

Amplification of miacc1 and miacc2

Reverse transcription of RNA from ripe mango fruit tissue was performed by using 1 μg total RNA and 2.5 U of Moloney Murine Leukemia Virus (MMLV) reverse transcriptase in a reaction mixture of 10 mM Tris-HCl, pH 8.3 containing 50 mM KCl, 5 mM $MgCl_2$, 1 mM of each dNTP, 1 U RNase inhibitor and 0.75 μM of oligonucleotide primer OLE-4 (Table 1). The reaction mixture was incubated for 30 min at 42° C. and then heated to 99° C. for 5 min to inactivate the reverse transcriptase. The cDNA produced was amplified with 2.5 U AmpliTaq DNA Polymerase in a reaction mixture of 10 mM Tris-HCl, pH 8.3 containing 2 mM $MgCl_2$, 50 mM KCl, and 0.15 μM of OLE-2 and OLE-4 (Table 1). After an initial 3 min denaturing period at 94° C., the PCR parameters were 1 min template denaturation at 94° C., 1 min primer annealing at 48° C. and 2 min primer extension at 72° C. for 45 cycles. A final extension step of 15 min at 72° C. was used subsequently to ensure full length amplification products.

The products of this PCR reaction were further amplified using a second set of oligonucleotide primers OLE-5 and OLE-6 (Table 1). The reaction consisted of adding to a tube a sample of the products obtained from the previous amplification and 2.5 U AmpliTaq DNA Polymerase in a reaction mixture of 10 mM Tris-HCl, pH 8.3 containing 1.5 mM $MgCl_2$, 50 mM KCl, 0.2 mM of each dNTP, 0.1% gelatin and 0.15 μM of each primer in a total volume of 100 μL. The PCR parameters were 30 sec template denaturation at 94° C., 30 sec primer annealing at 48° C. and 1.5 min primer extension at 72° C. for 30 cycles. The PCR products were analysed on 0.8% agarose gels and visualized with ethidium bromide.

Results:

After reverse transcription and PCR amplification, a DNA band of approximately 1.1 Kb could be observed in electrophoresis gels. The DNA fragment corresponding to this band was purified from the gel and subcloned into pBluescript. The analysis of several recombinant plasmids revealed the presence of two different inserts of approximately the same length but with different restriction patterns. The two different clones were named miacc1 (1096 bp) and miacc2 (1113 bp) respectively. The nucleotide and deduced amino acid sequences corresponding to miacc1 and miacc2 are shown respectively in FIG. 4 and FIG. 5. Comparison of these sequences with other published ACC synthase sequences indicates that miacc1 and miacc2 are cDNAs coding for members of the ACC synthase family in mango. Searches in all the available protein and DNA data banks failed to find 100% homology with any existing clone. The highest homology found for miacc1 was 71% at the DNA level with the inventor's previously published ACC synthase from mung bean (entry #Z11562 in the EMBL data bank), and 71% at the protein level with a petunia clone # S31450 in the PIR data base. The highest homology found for miacc2 was 73% at the DNA level respectively with a *Pelargonium hortorum* clone (entry #U17231 in the GenBank database) and a *Vigna radiate* mRNA clone (# Z11562, EMBL data bank). The highest homology found at the protein level for miacc2 was 77% with an ACC synthase from *Vigna radiata* (entry # S26214, PIR database).

Analysis of the miacc1 and miacc2 DNA sequences indicates that each of these sequences represents 75% of the coding region relating thereto.

EXAMPLE 4

Stable Integration and Expression of Acc Synthase Antisense Genes in Papaya (*Carica papaya* L.)

Materials and Methods

Initiation of somatic embryogenesis

Immature zygotic embryos are excised from green fruit of a high yielding papaya line, 90–100 days after pollination and are induced to form somatic embryos. Somatic embryos may be induced by placing zygotic embryos in solution culture consisting of 1/2MS (Murashige and Skoog, 1962, Physiologia Plantarum, 15, 473–497), 2 μM 6-benzylamino purine (BAP), 0.5 μM naphthaleneacetic acid (NAA), 400 μM adenine sulfate and 3% sucrose, pH 5.65 (Drew et al., 1994, In Current Issues in Plant Molecular and Cellular Biology, Proceedings of the VII International Congress on Plant Tissue Culture pp. 321–326, Florence, Italy) on an orbital shaker. Callused cotyledons are removed and discarded after 2–3 weeks. After a further 2 months on the shaker, the media are replaced with EM medium (1/2MS, 0.5 μM BAP, 0.05 μM NAA and 3% sucrose). Once secondary embryos are formed on this medium, they are multiplied approximately 10 fold on solid EM medium containing 0.8% Difco bactoagar (Drew et al., 1994, supra) and maintained on this medium.

Pretreatment of embryos

Somatic embryos are multiplied for three weeks in solid medium and cultured in liquid multiplication medium for three days prior to bombardment. Liquid medium pretreatment of somatic embryos can be performed by culturing embryos for 0–3 days in 30 mL of liquid EM medium at 70 rpm on an orbital shaker.

Transformation vector

A transformation vector which may be utilized for generation a transgenic variety of papaya, wherein expression of an ACC synthase enzyme is substantially inhibited, may be constructed by operably linking the nucleotide sequence of FIG. 2 or FIG. 3, in the antisense orientation, to the CaMV 35S promoter (or other suitable promoter) and to the nopaline synthase terminator region (or other suitable terminator sequence). The vector may also contain the kanamycin resistance gene as selectable marker.

Plasmid DNA for microprojectile bombardment can be purified by two cycles of caesium chloride-ethidium bromide density gradient centrifugation (Sambrook et al., 1989, supra).

Bombardment conditions

Embryos are bombarded using a particle inflow gun (Finer et al., 1992, Plant Cell Rep., 11, 323–328). Gold particles of 1.5–3 μm diameter (Aldrich) are used as microprojectiles wherein 120 mg of such gold particles are washed three times with 100% ethanol and three times with sterile water before suspension in 1 mL of sterile 50% glycerol. For preparation of microprojectiles, 25 μL of the gold suspension is mixed with 0.5 μg plasmid DNA, 25 μL 1 M $CaCl_2$, and 5 μL 0.1 M spermidine free base. All solutions are kept on ice.

The suspension is first sonicated and subsequently kept in suspension by occasional vortexing for 5 minutes. The suspension is then allowed to settle on ice for 10 minutes before 25 μL of the supernatant is moved and discarded. The remaining suspension is subsequently vortexed immediately before utilizing 4 μL of the mixture for each bombardment.

Embryos are arranged, without overlap, in an area of approximately 10 mm diameter. A protective baffle of stainless steel mesh with an aperture of 210 μm (Franks and Birch, 1991, Aus. J. Plant Physiol. 18, 471–480) is placed over the tissue during bombardment. The pressure of the helium blast is 500 kPa and the distance of the target embryos from the filter unit containing the coated gold particles is 7.5 to 10 cm.

Selection and regeneration of transformed plantlets

Following bombardment, somatic embryos are allowed to recover for 2 days on EM medium, prior to selection on EM medium containing kanamycin monosulfate (200 μg/mL). Embryos are then selected for kanamycin resistance after 3 to 5 months in such medium.

For germination, embryos are transferred to a modified de Fossard's medium (de Fossard et al., 1974, Physiologia Plantarum, 30, 125–130, as described by Drew and Miller, (1989, HortScience 64, 767–773), containing 25 μg/mL kanamycin. Single plantlets are then transferred into individual vessels containing single shoot medium (Drew and Smith, 1986, J. Hort. Sci., 61, 535–543) without kanamycin.

EXAMPLE 5

Stable Integration and Expression of ACC Synthase Antisense Genes in Mango (*Mangifera indica* L.)

Materials and Methods

Establishment of embryogenic cultures.

Embryogenic cultures are established according to procedures described by Dewald et al. (1989, Journal of the American Society of Horticultural Science 114, 712–716; Ibid, 114, 837–841). Immature fruits (4 to 6 cm) of especific mango cultivars (*M. indica* L.) are collected. Fruits are then surface-sterilized with 0.3% (wt/vol) sodium hypochlorite containing 2 to 3 drips of Tween 20 per 100 ml sterilant for 30 min, and subsequently rinsed thoroughly in sterile de-ionized water. Fruits are then bisected longitudinally and zygotic and nucellar embryos are excised and discarded. The ovule halves are then cultured so that the nucelli is in contact with a medium consisting of B5 major salts (Garnborg et al., 1968, Exp. Cell. Res., 50, 150–158), MS minor salts and organics (Murashige and Skoog, 1962, supra), supplemented with 6% (wt/vol) sucrose, 2.7 mM L-glutamine, and 4.5 μM 2,4-dichlorophenoxyacetic acid (2,4-D) (maintenance medium). The pH is then adjusted to 5.8 before addition of 0.17% gelrite (wt/vol) and the medium autoclaved at 120° C. at 1.1 $kgcm^{-2}$ for 15 min.

Explants are then transferred to fresh medium after 5 days, 10 days, and at 4-wk intervals thereafter. Proliferating nucellar proembryogenic masses are separated from ovule walls and cultured separately. These may be maintained on solid medium with a subculture interval of 30 days or in liquid medium of the same composition with a subculture interval of 5 days. All cultures on solid medium are kept in darkness at 25° C. Liquid cultures are maintained in the dark for 8 h and 16 h in diffused light (<0.2 $\mu molm^{-2}s^{-1}$) at 27° C. For *Agrobacterium tumefaciens* infection, actively growing proembryo masses in suspensions are used which have been derived from a 10-month-old culture maintained on solid medium.

Preparation of bacterial culture.

A single colony of *A. tumefaciens,* 9749ASE, from LB agar medium supplemented with 50 μg/ml kanamycin, 25 μg/ml chloramphenicol, and 100 μg/ml spectinomycin is inoculated into 5 mL of liquid broth of the same composition, at pH 7. After 16 h this is transferred to 50 mL of liquid broth of the same composition supplemented with 30 μM acetosyringone, pH 5.6, and incubated at 200 rpm for 16 h at 28° C.

Binary vectors can be constructed by operably linking the nucleotide sequence of FIG. 4 or FIG. 5, in the antisense orientation, to the CaMV 35S promoter (or other suitable promoter) and to the nopaline synthase terminator region (or other suitable terminator sequence) between the left and the right borders. The vector may also contain the NOS-NPTII-NOS chimeric kanamycin resistance gene between the left and the right borders for selection of transformed plant cells.

The recombinant plasmid is introduced into Agrobacterium by triparental mating.

Co-cultivation of mango proembryos with *A. tumefaciens.* Three grams of proembryo masses of size <1000 mm diameter maintained in liquid medium are lightly macerated and cultured in 50 mL of liquid maintenance medium to which 0.05 mL of a log phase culture of acetosyringone-activated *A. tumefaciens* are added. Flasks are maintained on a rotary shaker at 120 rpm. Proembryos are then transferred to fresh maintenance medium every 24 h for 3 days. No additional bacterium is added at this stage.

Selection protocols.

The main criterium used for identification of transformants is the ability of proembryos to grow in liquid selection medium. The kanamycin levels that are used for the selection are based on earlier studies on kanamycin sensitivity of mango somatic embryos (Mathews and Litz, 1990, HortScience, 25, 965–966).

After 3 days of co-cultivation, the proembryo masses are selected using a stepwise selection protocol.

Step 1: Proembryos are evenly plated on solid maintenance medium with 200 μg/mL kanamycin and 500 μg/mL cefotaxime (10–12 months).

Step 2: Proembryos are more stringently selected on solid medium at 400 μg/mL kanamycin for increasing the proportion of transformed versus non-transformed cells (2 months).

Step 3: Proembryos are subcultured in liquid maintenance medium with 100 μg/mL kanamycin (2–3 months).

Proembryos on solid medium are then subcultured onto the same medium every 3 wk for 10 months, and thereafter maintained on selection medium without cefotaxine.

Recovery of transformed somatic embryos.

Proembryos from liquid selection medium are transferred to liquid embryogenesis medium (maintenance medium without 2,4-D. supplemented with 0.22 μM benzylaminopurine) containing 100 μg/mL kanamycin for 30 to 50 days for somatic embryo development.

All cultures in liquid selection medium are transferred subsequently at 3- to 5-day intervals to fresh medium, depending on the amount of darkening that has occurred due to oxidation.

The DNA sequences of the invention have utility as targets for the generation of transgenic variants of pineapple, papaya and mango in which the expression of ACC synthase is substantially inhibited to effect suppression of fruit senescence.

Suitable methods for engineering such transgenic plants which have been described above could be utilized to engineer such transgenic plants. The use of such methods, in concert with the DNA sequences of the invention, will enable the generation or ripening-resistant varieties of pineapple, papaya and mango. It is anticipated that, in comparison to normal varieties of these fruits, the quality, quantity and longevity of the transgenic varieties will be greatly improved for market in both developed and undeveloped countries.

TABLE 1

| Degenerate olgonucleotides designed to amplify ACC synthase genes and cDNAs from higher plants. | | |
|---|---|---|
| Ez-2 | SEQ ID NO:11 | 5' TA(C/T)TT(C/T)GA(C/T)GG(A/C/G/T)TGGAA(A/G)GC 3' |
| Ez-4 | SEQ ID NO:12 | 5' TC(A/G)TCCAT(A/G)TT(A/C/G/T)GC(A/G)AA(A/G)CA 3' |
| Ez-5 | SEQ ID NO:13 | 5' CA(A/G)TGGG(A/C/G/T)(C/T)T(A/C/G/T)GC(A/C/G/T)GA(A/G)AA 3' |
| Ez-6 | SEQ ID NO:14 | 5' GC(A/G)AA(A/G)CA(A/C/G/T)AC(A/C/G/T)C(G/T)(A/G)AACCA 3' |
| Ez-7 | SEQ ID NO:15 | 5' AC(A/C/G/T)C(G/T)(A/G)AACCA(A/C/G/T)CC(A/C/G/T)GG(C/T)TC 3' |
| OLE-2 | SEQ ID NO:16 | 5' GCTCTAGATA(C/T)TT(C/T)GA(C/T)GC(A/C/G/T)TGGAA(A/G)GC 3' |
| OLE-4 | SEQ ID NO:17 | 5' GCGAATTC(A/G)TCCAT(A/G)TT(A/C/G/T)GC(A/G)AA(A/G)CA 3' |
| OLE-5 | SEQ ID NO:18 | 5' CCTGATCA(A/G)ATGGG(A/C/G/T)(C/T)T(A/C/G/T)GC(A/C/G/T)GA(A/G)AA 3' |
| OLE-6 | SEQ ID NO:19 | 5' CTCTGCAGC(A/G)AA(A/G)AA(A/C/G/T)AC(A/C/G/T)C(G/T)(A/G)AACCA 3' |

What is claimed is:

1. An isolated nucleotide sequence which is of sufficient complementarity to an endogenous ACC synthase gene to reduce expression of said endogenous ACC synthase gene, and which hybridizes under high stringency conditions with SEQ ID NO:1, wherein the high stringency conditions are selected from the group consisting of:

(i) 0.1×SSC/0.1% SDS at about 68° C. for at least about 20 minutes; and (ii) 0.2×SSC/0.1% SDS at about 68° C. for about one hour.

2. An isolated nucleotide sequence which is of sufficient complementarity to an endogenous ACC synthase gene to reduce expression of said endogenous ACC synthase gene, and which hybridizes under high stringency conditions with SEQ ID NO:5, wherein the high stringency conditions are selected from the group consisting of:

(i) 0.1×SSC/0.1% SDS at about 68° C. for at least about 20 minutes; and (ii) 0.2×SSC/0.1% SDS at about 68° C. for about one hour.

3. A method producing a transgenic papaya plant with inhibited fruit senescence including the steps of:

(a) introducing into a papaya plant, plant part or plant cell a vector comprising an isolated nucleotide sequence which is of sufficient complementarity to an endogenous ACC synthase gene to reduce expression of said endogenous ACC synthase gene, and which hybridises with SEQ ID NO:5 under high stringency conditions selected from the group consisting of:

(i) 0.1×SSC/0.1% SDS at about 68° C. for at least about 20 minutes;

(ii) 0.2×SSC/0.1% SDS at about 68° C. for about one hour;

wherein said isolated nucleotide sequence is operably linked, in a sense orientation, to one or more regulatory nucleotide sequences; and (b) growing said plant, or regenerating said plant part or said plant cell to produce the transgenic papaya plant.

4. A method of producing a transgenic papaya plant with inhibited fruit senescence including the steps of:

(a) introducing into a papaya plant, plant part or plant cell a vector comprising an isolated nucleotide sequence which is of sufficient complementarity to an endogenous ACC synthase gene to reduce expression of said endogenous ACC synthase gene, and which hybridises with SEQ ID NO:5 under high stringency conditions selected from the group consisting of:

(i) 0.1×SSC/0.1% SDS at about 68° C. for at least about 20 minutes;

(ii) 0.2×SSC/0.1% SDS at about 68° C. for about one hour;

wherein said nucleotide sequence is operably linked, in an antisense orientation, to one or more regulatory nucleotide sequences; and (b) growing said plant, or regenerating said plant part or said plant cell to produce the transgenic papaya plant.

5. An isolated nucleotide sequence which is of sufficient complementarity to an endogenous ACC synthase gene to reduce expression of said endogenous ACC synthase gene, and which hybridizes under high stringency conditions with SEQ ID NO:7 or SEQ ID NO:9, wherein the high stringency conditions are selected from the group consisting of:

(i) 0.1×SSC/0.1% SDS at about 68° C. for at least about 20 minutes; and (ii) 0.2×SSC/0.1% SDS at about 68° C. for about one hour.

6. A method of producing a transgenic mango plant with inhibited fruit senescence comprising:

(a) introducing into a mango plant, plant part or plant cell a vector comprising an isolated nucleotide sequence which is of sufficient complementarity to an endogenous ACC synthase gene to reduce expression of said endogenous ACC synthase gene, and which hybridises with SEQ ID NO:7 or SEQ ID NO:9 under high stringency conditions selected from the group consisting of:

(i) 0.1×SSC/0.1% SDS at about 68° C. for at least about 20 minutes;

(ii) 0.2×SSC/0.1% SDS at about 68° C. for about one hour;

wherein said nucleotide sequence is operably linked, in a sense orientation, to one or more regulatory nucleotide sequences; and (b) growing said plant, or regenerating said plant part or said plant cell to produce the transgenic mango plant.

7. A method of producing a transgenic mango plant with inhibited fruit senescence including the steps of:

(a) introducing into a mango plant, plant part or plant cell a vector comprising an isolated nucleotide sequence which is of sufficient complementarity to an endogenous ACC synthase gene to reduce expression of said endogenous ACC synthase gene, and which hybridises with SEQ ID NO:7 or SEQ ID NO:9 under high stringency conditions selected from the group consisting of:

(i) 0.1×SSC/0.1% SDS at about 68° C. for at least about 20 minutes;

(ii) 0.2×SSC/0.1% SDS at about 68° C. for about one hour;

wherein said nucleotide sequence is operably linked, in an antisense orientation, to one or more regulatory nucleotide sequences; and (b) growing said plant, or regenerating said plant part or said plant cell to produce the transgenic mango plant.

8. A vector comprising at least one copy of an isolated nucleotide sequence which is of sufficient complementarity to an endogenous ACC synthase gene to reduce expression of said endogenous ACC synthase gene, and which hybridises under high stringency conditions with SEQ ID NO:1, SEQ ID NO: 5, SEQ ID NO:7 or SEQ ID NO: 9, wherein the high stringency conditions are selected from the group consisting of:

(i) 0.1×SSC/0.1% SDS at about 68° C. for at least about 20 minutes; and (ii) 0.2×SSC/0.1% SDS at about 68° C. for about one hour.

9. The vector of claim 8 wherein said nucleotide sequence is operably linked to at least one regulatory nucleotide sequence.

* * * * *

```
                              SEQUENCE LISTING


(1) GENERAL INFORMATION:

   (iii) NUMBER OF SEQUENCES: 19


(2) INFORMATION FOR SEQ ID NO: 1:

     (i) SEQUENCE CHARACTERISTICS:
          (A) LENGTH: 1080 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 1..1080

    (xi) SEQUENCE DESCRIPTION: SEQ ID NO: 1:

CAG ATG GGG TTT GCG GAG AAC CAG CTT TCG CTG GAG TTA ATA CGT GAG        48
Gln Met Gly Phe Ala Glu Asn Gln Leu Ser Leu Glu Leu Ile Arg Glu
  1               5                  10                  15

TGG ATC AAG AAT CAC CCG GAG GCC TCC ATT TGC TCG GCG GAG GGC CTG        96
Trp Ile Lys Asn His Pro Glu Ala Ser Ile Cys Ser Ala Glu Gly Leu
             20                  25                  30

CCG CAG TTC ATG GAG ATC GCC AAT TTC CAA GAC TAC CAT GGC TTG CCG       144
Pro Gln Phe Met Glu Ile Ala Asn Phe Gln Asp Tyr His Gly Leu Pro
         35                  40                  45

GCT TTT CTG CAG GGA ATC GCG AAA TTG ATG GAG AAA GTG AGA GGA GGA       192
Ala Phe Leu Gln Gly Ile Ala Lys Leu Met Glu Lys Val Arg Gly Gly
     50                  55                  60

AGG GTC AAA TTC GAT CCG AAC CGC GTG GTG ATG AGC GGC GGA GGC ACT       240
Arg Val Lys Phe Asp Pro Asn Arg Val Val Met Ser Gly Gly Gly Thr
 65                  70                  75                  80

GGA GCG CAA GAA ACG CTC GCG TTT TGT CTC GCT GAC CCT GGC GAC GCC       288
Gly Ala Gln Glu Thr Leu Ala Phe Cys Leu Ala Asp Pro Gly Asp Ala
                 85                  90                  95

TTC CTC GTC CCA ACT CCG TAC TAT CCA GCA TTT AAT CGC GAT CTC CGG       336
Phe Leu Val Pro Thr Pro Tyr Tyr Pro Ala Phe Asn Arg Asp Leu Arg
            100                 105                 110

TGG AGA ACG GGC GTC GAG CTC CTC CCG GTT CAC TGC AAG AGC TCT AAT       384
Trp Arg Thr Gly Val Glu Leu Leu Pro Val His Cys Lys Ser Ser Asn
```

-continued

```
        115                 120                 125

CAC TTC AGA GTC ACC AAA ACG GCG CTA GAA TCG GCA TAC GAG AAG GCG       432
His Phe Arg Val Thr Lys Thr Ala Leu Glu Ser Ala Tyr Glu Lys Ala
    130                 135                 140

CGA AAG GAT AAC ATC AGA GTA AAA GGA GTA CTG ATA ACC AAC CCA TCC       480
Arg Lys Asp Asn Ile Arg Val Lys Gly Val Leu Ile Thr Asn Pro Ser
145                 150                 155                 160

AAC CCG CTC GGC ACG ACC ATG GAT AAA CAC ACG CTA CAG ACC CTC GTG       528
Asn Pro Leu Gly Thr Thr Met Asp Lys His Thr Leu Gln Thr Leu Val
                165                 170                 175

AAA TTC GTA AAC GAA AGG AGA ATC CAC CTA GTC TGC GAC GAG TTA TAC       576
Lys Phe Val Asn Glu Arg Arg Ile His Leu Val Cys Asp Glu Leu Tyr
            180                 185                 190

GGC GCA ACC ATC TTT AGG GAG CCC AGG TTC GTC AGC ATC TCC GAG GTA       624
Gly Ala Thr Ile Phe Arg Glu Pro Arg Phe Val Ser Ile Ser Glu Val
        195                 200                 205

ATA GAA GAG GAC CCG AAC TGC GAC AAG AAT CTG ATC CAC ATT GCG TAC       672
Ile Glu Glu Asp Pro Asn Cys Asp Lys Asn Leu Ile His Ile Ala Tyr
    210                 215                 220

AGT CTC TCA AAG GAC TTC GGT CTC CCC GGA TTC CGA GTC GGG ATC GTG       720
Ser Leu Ser Lys Asp Phe Gly Leu Pro Gly Phe Arg Val Gly Ile Val
225                 230                 235                 240

TAT TCC TAC AAC GAC ACG GTG GTT AGT TGC GCA CGC AGA ATG TCG AGC       768
Tyr Ser Tyr Asn Asp Thr Val Val Ser Cys Ala Arg Arg Met Ser Ser
                245                 250                 255

TTC GGC CTC GTC TCG TCG CAG ACA CAG TAC CTA CTG GCC GCC ATG CTA       816
Phe Gly Leu Val Ser Ser Gln Thr Gln Tyr Leu Leu Ala Ala Met Leu
            260                 265                 270

TCC GGC GAA GAA TTT TTG CCA ACA TTA CTG ACT GAA AGC GCG AAG AGT       864
Ser Gly Glu Glu Phe Leu Pro Thr Leu Leu Thr Glu Ser Ala Lys Ser
        275                 280                 285

CTG TCG GAG AGC CAC AGG ATC TTC TCT TCC GGC CTT GAG GAA GTC GAC       912
Leu Ser Glu Ser His Arg Ile Phe Ser Ser Gly Leu Glu Glu Val Asp
    290                 295                 300

ATC CGC TGC TTG GAC GGC AAT GCC GGG GTC TTC TGC TGG ATG GAC CTA       960
Ile Arg Cys Leu Asp Gly Asn Ala Gly Val Phe Cys Trp Met Asp Leu
305                 310                 315                 320

CGG CAC CTC CTC AAA GAA GCC ACC GAA GAC GGC GAG CTC GAG CTG TGG      1008
Arg His Leu Leu Lys Glu Ala Thr Glu Asp Gly Glu Leu Glu Leu Trp
                325                 330                 335

CGC GTG ATA GTG AAC AAT GTC AAG CTC AAT GTG TCC CCC GGT TCG TCG      1056
Arg Val Ile Val Asn Asn Val Lys Leu Asn Val Ser Pro Gly Ser Ser
            340                 345                 350

TTT TAT TGC GCC GAG CCA GGT TGG                                      1080
Phe Tyr Cys Ala Glu Pro Gly Trp
        355                 360
```

(2) INFORMATION FOR SEQ ID NO: 2:

(i) SEQUENCE CHARACTERISTICS:
(A) LENGTH: 360 amino acids
(B) TYPE: amino acid
(D) TOPOLOGY: linear (ii) MOLECULE TYPE: protein (xi) SEQUENCE DESCRIPTION: SEQ ID NO: 2:

```
Gln Met Gly Phe Ala Glu Asn Gln Leu Ser Leu Glu Leu Ile Arg Glu
  1               5                  10                  15

Trp Ile Lys Asn His Pro Glu Ala Ser Ile Cys Ser Ala Glu Gly Leu
             20                  25                  30
```

-continued

```
Pro Gln Phe Met Glu Ile Ala Asn Phe Gln Asp Tyr His Gly Leu Pro
         35                  40                  45

Ala Phe Leu Gln Gly Ile Ala Lys Leu Met Glu Lys Val Arg Gly Gly
     50                  55                  60

Arg Val Lys Phe Asp Pro Asn Arg Val Val Met Ser Gly Gly Gly Thr
 65                  70                  75                  80

Gly Ala Gln Glu Thr Leu Ala Phe Cys Leu Ala Asp Pro Gly Asp Ala
                 85                  90                  95

Phe Leu Val Pro Thr Pro Tyr Tyr Pro Ala Phe Asn Arg Asp Leu Arg
            100                 105                 110

Trp Arg Thr Gly Val Glu Leu Leu Pro Val His Cys Lys Ser Ser Asn
        115                 120                 125

His Phe Arg Val Thr Lys Thr Ala Leu Glu Ser Ala Tyr Glu Lys Ala
    130                 135                 140

Arg Lys Asp Asn Ile Arg Val Lys Gly Val Leu Ile Thr Asn Pro Ser
145                 150                 155                 160

Asn Pro Leu Gly Thr Thr Met Asp Lys His Thr Leu Gln Thr Leu Val
                165                 170                 175

Lys Phe Val Asn Glu Arg Arg Ile His Leu Val Cys Asp Glu Leu Tyr
            180                 185                 190

Gly Ala Thr Ile Phe Arg Glu Pro Arg Phe Val Ser Ile Ser Glu Val
        195                 200                 205

Ile Glu Glu Asp Pro Asn Cys Asp Lys Asn Leu Ile His Ile Ala Tyr
    210                 215                 220

Ser Leu Ser Lys Asp Phe Gly Leu Pro Gly Phe Arg Val Gly Ile Val
225                 230                 235                 240

Tyr Ser Tyr Asn Asp Thr Val Val Ser Cys Ala Arg Arg Met Ser Ser
                245                 250                 255

Phe Gly Leu Val Ser Ser Gln Thr Gln Tyr Leu Leu Ala Ala Met Leu
            260                 265                 270

Ser Gly Glu Glu Phe Leu Pro Thr Leu Leu Thr Glu Ser Ala Lys Ser
        275                 280                 285

Leu Ser Glu Ser His Arg Ile Phe Ser Ser Gly Leu Glu Glu Val Asp
    290                 295                 300

Ile Arg Cys Leu Asp Gly Asn Ala Gly Val Phe Cys Trp Met Asp Leu
305                 310                 315                 320

Arg His Leu Leu Lys Glu Ala Thr Glu Asp Gly Glu Leu Glu Leu Trp
                325                 330                 335

Arg Val Ile Val Asn Asn Val Lys Leu Asn Val Ser Pro Gly Ser Ser
            340                 345                 350

Phe Tyr Cys Ala Glu Pro Gly Trp
        355                 360
```

(2) INFORMATION FOR SEQ ID NO: 3:

(i) SEQUENCE CHARACTERISTICS:
- (A) LENGTH: 1104 base pairs
- (B) TYPE: nucleic acid
- (C) STRANDEDNESS: single
- (D) TOPOLOGY: linear (ii) MOLECULE TYPE: cDNA (ix) FEATURE:
- (A) NAME/KEY: CDS
- (B) LOCATION: 1..1104

(xi) SEQUENCE DESCRIPTION: SEQ ID NO: 3:

```
CAG ATG GGC CTT GCT GAG AAT CAG CTT TGC TTT AAT TTA ATT CAC GAG        48
Gln Met Gly Leu Ala Glu Asn Gln Leu Cys Phe Asn Leu Ile His Glu
  1               5                  10                  15

TGG CCG CTG AAA AAC CCA GAA GCC TCC ATT TGT ACA ACA CAA GGA GCA        96
Trp Pro Leu Lys Asn Pro Glu Ala Ser Ile Cys Thr Thr Gln Gly Ala
             20                  25                  30

GCT GAA TTC AGA GAT ATA GCT ATC TTT CAA GAT TAT CAT GGC TTG GCT       144
Ala Glu Phe Arg Asp Ile Ala Ile Phe Gln Asp Tyr His Gly Leu Ala
         35                  40                  45

GAA TTC AGA GAG GCT GTT GCA AAG TTT ATG GGG AAA GTG AGA AGA AAC       192
Glu Phe Arg Glu Ala Val Ala Lys Phe Met Gly Lys Val Arg Arg Asn
     50                  55                  60

AGA GCT TCA TTT GAC CCT GAT CGG ATT GTT ATG AGT GGA GGA GCA ACT       240
Arg Ala Ser Phe Asp Pro Asp Arg Ile Val Met Ser Gly Gly Ala Thr
 65                  70                  75                  80

GGA GCT CAT GAA ATG ATT GGT TTC TGT TTG GCT GAT CCT GGC GAT GCA       288
Gly Ala His Glu Met Ile Gly Phe Cys Leu Ala Asp Pro Gly Asp Ala
                 85                  90                  95

TTC TTG GTT CCA ACT CCT TAT TAT CCA GGG TTT GAT AGA GAT TTG AGA       336
Phe Leu Val Pro Thr Pro Tyr Tyr Pro Gly Phe Asp Arg Asp Leu Arg
            100                 105                 110

TGG AGA ACG GGA GTC AAA CTC ATT CCA GTT GTC TGT GAA AGC TCA AAC       384
Trp Arg Thr Gly Val Lys Leu Ile Pro Val Val Cys Glu Ser Ser Asn
        115                 120                 125

GAT TAC CAG ATC ACC ATA GAA GCC CTG GAA GCT GCT TAT GAA ACC GCA       432
Asp Tyr Gln Ile Thr Ile Glu Ala Leu Glu Ala Ala Tyr Glu Thr Ala
    130                 135                 140

CAA GAA GCT GAC ATC AAG GTA AAG GGT TTG GTC ATA ACC AAC CCA TCA       480
Gln Glu Ala Asp Ile Lys Val Lys Gly Leu Val Ile Thr Asn Pro Ser
145                 150                 155                 160

AAC CCA CTG GGA ACA ATT ATT ACC AAG GAC ACA TTA GAA GCT CTA GTC       528
Asn Pro Leu Gly Thr Ile Ile Thr Lys Asp Thr Leu Glu Ala Leu Val
                165                 170                 175

ACC TTC ACC AAC CAC AAG AAC ATT CAT CTG GTG TGT GAT GAG ATA TAT       576
Thr Phe Thr Asn His Lys Asn Ile His Leu Val Cys Asp Glu Ile Tyr
            180                 185                 190

GCT GGT TAC CGT CTT CAG CCC AGG GCC GAA TTC ACC AGC ATA GCC GAG       624
Ala Gly Tyr Arg Leu Gln Pro Arg Ala Glu Phe Thr Ser Ile Ala Glu
        195                 200                 205

ATA ATT GAA GAA GAT AAA ATT TGT TGC AAT CGT GAT CTC ATC CAC ATC       672
Ile Ile Glu Glu Asp Lys Ile Cys Cys Asn Arg Asp Leu Ile His Ile
    210                 215                 220

ATT TAC AGT TTA TCC AAA GAC ATG GGA TTC CCT GGA TTT AGA GTT GGC       720
Ile Tyr Ser Leu Ser Lys Asp Met Gly Phe Pro Gly Phe Arg Val Gly
225                 230                 235                 240

ATT GTG TAT TCA TAC AAT GAT GCA GTG GTG AGT TGT GCT CGT AAG ATG       768
Ile Val Tyr Ser Tyr Asn Asp Ala Val Val Ser Cys Ala Arg Lys Met
                245                 250                 255

TCG AGC TTC GGC CTA GTA TCT TCG CAA ACC CAG TAT CTG ATT GCA TCC       816
Ser Ser Phe Gly Leu Val Ser Ser Gln Thr Gln Tyr Leu Ile Ala Ser
            260                 265                 270

ATG TTA GCA GAC GAT GAA TTT GTA GAC AAA TTT ATT GTA GAG AGC AGA       864
Met Leu Ala Asp Asp Glu Phe Val Asp Lys Phe Ile Val Glu Ser Arg
        275                 280                 285

AAG AGG CTG GCA ATG AGA CAT AGT TTT TTC ACA CAA AGA CTT GCT CAA       912
Lys Arg Leu Ala Met Arg His Ser Phe Phe Thr Gln Arg Leu Ala Gln
    290                 295                 300

GTA GGC ATT AAC TGT TTA AAA AGC AAT GCT GGT CTT TTT GTG TGG ATG       960
```

-continued

```
Val Gly Ile Asn Cys Leu Lys Ser Asn Ala Gly Leu Phe Val Trp Met
305                 310                 315                 320

GAT TTG CGT AGA CTG CTG AAA GAA CAG ACA TTT GAA GCA GAA ATG GTG     1008
Asp Leu Arg Arg Leu Leu Lys Glu Gln Thr Phe Glu Ala Glu Met Val
                325                 330                 335

TTA TGG AGA GTA ATT ATA AAC GAA ATG AAA CTC AAT GTA TCT CCT GGT     1056
Leu Trp Arg Val Ile Ile Asn Glu Met Lys Leu Asn Val Ser Pro Gly
            340                 345                 350

TCG TCT TTC CAC TGC TCA GAA CCT GGC TGG TTC AGC GTC TGC TTC GCT     1104
Ser Ser Phe His Cys Ser Glu Pro Gly Trp Phe Ser Val Cys Phe Ala
        355                 360                 365
```

(2) INFORMATION FOR SEQ ID NO: 4:

(i) SEQUENCE CHARACTERISTICS:
(A) LENGTH: 368 amino acids
(B) TYPE: amino acid
(D) TOPOLOGY: linear (ii) MOLECULE TYPE: protein (xi) SEQUENCE DESCRIPTION: SEQ ID NO: 4:

```
Gln Met Gly Leu Ala Glu Asn Gln Leu Cys Phe Asn Leu Ile His Glu
  1               5                  10                  15

Trp Pro Leu Lys Asn Pro Glu Ala Ser Ile Cys Thr Thr Gln Gly Ala
             20                  25                  30

Ala Glu Phe Arg Asp Ile Ala Ile Phe Gln Asp Tyr His Gly Leu Ala
         35                  40                  45

Glu Phe Arg Glu Ala Val Ala Lys Phe Met Gly Lys Val Arg Arg Asn
     50                  55                  60

Arg Ala Ser Phe Asp Pro Asp Arg Ile Val Met Ser Gly Gly Ala Thr
 65                  70                  75                  80

Gly Ala His Glu Met Ile Gly Phe Cys Leu Ala Asp Pro Gly Asp Ala
                 85                  90                  95

Phe Leu Val Pro Thr Pro Tyr Tyr Pro Gly Phe Asp Arg Asp Leu Arg
            100                 105                 110

Trp Arg Thr Gly Val Lys Leu Ile Pro Val Val Cys Glu Ser Ser Asn
        115                 120                 125

Asp Tyr Gln Ile Thr Ile Glu Ala Leu Glu Ala Ala Tyr Glu Thr Ala
    130                 135                 140

Gln Glu Ala Asp Ile Lys Val Lys Gly Leu Val Ile Thr Asn Pro Ser
145                 150                 155                 160

Asn Pro Leu Gly Thr Ile Ile Thr Lys Asp Thr Leu Glu Ala Leu Val
                165                 170                 175

Thr Phe Thr Asn His Lys Asn Ile His Leu Val Cys Asp Glu Ile Tyr
            180                 185                 190

Ala Gly Tyr Arg Leu Gln Pro Arg Ala Glu Phe Thr Ser Ile Ala Glu
        195                 200                 205

Ile Ile Glu Glu Asp Lys Ile Cys Cys Asn Arg Asp Leu Ile His Ile
    210                 215                 220

Ile Tyr Ser Leu Ser Lys Asp Met Gly Phe Pro Gly Phe Arg Val Gly
225                 230                 235                 240

Ile Val Tyr Ser Tyr Asn Asp Ala Val Val Ser Cys Ala Arg Lys Met
                245                 250                 255

Ser Ser Phe Gly Leu Val Ser Ser Gln Thr Gln Tyr Leu Ile Ala Ser
            260                 265                 270

Met Leu Ala Asp Asp Glu Phe Val Asp Lys Phe Ile Val Glu Ser Arg
```

-continued

```
        275                 280                 285

Lys Arg Leu Ala Met Arg His Ser Phe Phe Thr Gln Arg Leu Ala Gln
    290                 295                 300

Val Gly Ile Asn Cys Leu Lys Ser Asn Ala Gly Leu Phe Val Trp Met
305                 310                 315                 320

Asp Leu Arg Arg Leu Leu Lys Glu Gln Thr Phe Glu Ala Glu Met Val
                325                 330                 335

Leu Trp Arg Val Ile Ile Asn Glu Met Lys Leu Asn Val Ser Pro Gly
            340                 345                 350

Ser Ser Phe His Cys Ser Glu Pro Gly Trp Phe Ser Val Cys Phe Ala
        355                 360                 365


(2) INFORMATION FOR SEQ ID NO: 5:

     (i) SEQUENCE CHARACTERISTICS:
          (A) LENGTH: 1098 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 1..1098

    (xi) SEQUENCE DESCRIPTION: SEQ ID NO: 5:

CAG ATG GGT TTT GCT GAA AAT CAG CTT TGC TTT GAT TTG ATC GAG AAG       48
Gln Met Gly Phe Ala Glu Asn Gln Leu Cys Phe Asp Leu Ile Glu Lys
  1               5                  10                  15

TGG GTT AAA AAG AAT CCC AAT GCT TCC ATC TGC ACA GCT GAA GGG GTT       96
Trp Val Lys Lys Asn Pro Asn Ala Ser Ile Cys Thr Ala Glu Gly Val
             20                  25                  30

GAA AAC TTC AAG CAC ATA GCC AAC TTC CAA GAC TAT CAT GGC CTG AAA      144
Glu Asn Phe Lys His Ile Ala Asn Phe Gln Asp Tyr His Gly Leu Lys
         35                  40                  45

GAA TTT AGA CAG GAA GTT GCC AAG TTA ATG GGG AAG GCA AGA GGC GGC      192
Glu Phe Arg Gln Glu Val Ala Lys Leu Met Gly Lys Ala Arg Gly Gly
     50                  55                  60

AGA GTG ACG TTC GAC CCA GAG CGT ATT GTG ATG AGC GGG GGA GCG ACA      240
Arg Val Thr Phe Asp Pro Glu Arg Ile Val Met Ser Gly Gly Ala Thr
 65                  70                  75                  80

GGC GCC AGC GAG ACG ATT ATG TTT TGC TTG GCG GAT CCA GGC GAT GCT      288
Gly Ala Ser Glu Thr Ile Met Phe Cys Leu Ala Asp Pro Gly Asp Ala
                 85                  90                  95

CTT CTG GTT CCC ACT CCT TAC TAT CCT GGA TTC AAT AGG GAC CTG AGA      336
Leu Leu Val Pro Thr Pro Tyr Tyr Pro Gly Phe Asn Arg Asp Leu Arg
            100                 105                 110

TGG CGA ACC GGC GTC CAG ATT ATT CCC GTG CAA TGC AGC AGC TCA CAC      384
Trp Arg Thr Gly Val Gln Ile Ile Pro Val Gln Cys Ser Ser Ser His
        115                 120                 125

AAT TTT ACA GTA ACA CGG GAA GCC GTA GAG GCT GCG TAC CAG AAA GCT      432
Asn Phe Thr Val Thr Arg Glu Ala Val Glu Ala Ala Tyr Gln Lys Ala
    130                 135                 140

CAA GAA GCC AAC ATC AAT GTC ACA GGC TTG ATC ATC ACC AAC CCC TCG      480
Gln Glu Ala Asn Ile Asn Val Thr Gly Leu Ile Ile Thr Asn Pro Ser
145                 150                 155                 160

AAT CCG CTA GGC ACC ACC TTA GAC TCA CAA ACA CTC CAG AGC TTG GTC      528
Asn Pro Leu Gly Thr Thr Leu Asp Ser Gln Thr Leu Gln Ser Leu Val
                165                 170                 175

ATC TTC GTC AAC GAC AAG ACC ATC CAC CTG GTC TGC GAC GAA ATC TAT      576
```

-continued

```
Ile Phe Val Asn Asp Lys Thr Ile His Leu Val Cys Asp Glu Ile Tyr
            180                 185                 190

GCC GCC ACC GTC TTC AGC TCC CCG GAG TTC GTC AGC ATC GGG GAG ATC      624
Ala Ala Thr Val Phe Ser Ser Pro Glu Phe Val Ser Ile Gly Glu Ile
        195                 200                 205

ATC CAA GAA ATG GAC GTC AAC CGC GAC CTT ATC CAC ATC ATC TAC AGC      672
Ile Gln Glu Met Asp Val Asn Arg Asp Leu Ile His Ile Ile Tyr Ser
    210                 215                 220

TTG TCC AAA GAT ATG GGT CTC CCC GGT TTC CGG GTA GGT ATT GTG TAT      720
Leu Ser Lys Asp Met Gly Leu Pro Gly Phe Arg Val Gly Ile Val Tyr
225                 230                 235                 240

TCC TAC AAC GAC GGT GTA TTA AGC TGC GGC CGG CGG ATG TCG AGC TTT      768
Ser Tyr Asn Asp Gly Val Leu Ser Cys Gly Arg Arg Met Ser Ser Phe
                245                 250                 255

GGG TTG GTC TCG TCA CAG ACT CAA TAT TTC CTG GCG ACA CTG CTG TCC      816
Gly Leu Val Ser Ser Gln Thr Gln Tyr Phe Leu Ala Thr Leu Leu Ser
            260                 265                 270

GAC GAC GAG TTC GTC GAT TAC TTC CTC CGG GAA AGC TCG AAG AGG CTG      864
Asp Asp Glu Phe Val Asp Tyr Phe Leu Arg Glu Ser Ser Lys Arg Leu
        275                 280                 285

GCG AGA AGA CAC CAT AAA CTC ACC AGA GGG CTG GAG CAA GTG GGG ATA      912
Ala Arg Arg His His Lys Leu Thr Arg Gly Leu Glu Gln Val Gly Ile
    290                 295                 300

AAG TGC TTG AAA AGC AAT GCC GGA CTT TTT GTG TGG ATG GAC CTG CGG      960
Lys Cys Leu Lys Ser Asn Ala Gly Leu Phe Val Trp Met Asp Leu Arg
305                 310                 315                 320

AGG CTC CTG GAA GGT CCA ACG TCG TTT GAT GCA GAA ATG AAG CTG TGG     1008
Arg Leu Leu Glu Gly Pro Thr Ser Phe Asp Ala Glu Met Lys Leu Trp
                325                 330                 335

CGG ACC ATC GTC AAC GAC GTG AAG CTG AAC GTG TCG CCG GGA TCT TCG     1056
Arg Thr Ile Val Asn Asp Val Lys Leu Asn Val Ser Pro Gly Ser Ser
            340                 345                 350

TTC CAC GTG GCG GAG CCG GGG TGG TTC AGA GTA TGT TTC GCT             1098
Phe His Val Ala Glu Pro Gly Trp Phe Arg Val Cys Phe Ala
        355                 360                 365
```

(2) INFORMATION FOR SEQ ID NO: 6:

(i) SEQUENCE CHARACTERISTICS:
(A) LENGTH: 366 amino acids
(B) TYPE: amino acid
(D) TOPOLOGY: linear (ii) MOLECULE TYPE: protein (xi) SEQUENCE DESCRIPTION: SEQ ID NO: 6:

```
Gln Met Gly Phe Ala Glu Asn Gln Leu Cys Phe Asp Leu Ile Glu Lys
  1               5                  10                  15

Trp Val Lys Lys Asn Pro Asn Ala Ser Ile Cys Thr Ala Glu Gly Val
             20                  25                  30

Glu Asn Phe Lys His Ile Ala Asn Phe Gln Asp Tyr His Gly Leu Lys
        35                  40                  45

Glu Phe Arg Gln Glu Val Ala Lys Leu Met Gly Lys Ala Arg Gly Gly
    50                  55                  60

Arg Val Thr Phe Asp Pro Glu Arg Ile Val Met Ser Gly Gly Ala Thr
 65                  70                  75                  80

Gly Ala Ser Glu Thr Ile Met Phe Cys Leu Ala Asp Pro Gly Asp Ala
                 85                  90                  95

Leu Leu Val Pro Thr Pro Tyr Tyr Pro Gly Phe Asn Arg Asp Leu Arg
            100                 105                 110
```

```
Trp Arg Thr Gly Val Gln Ile Ile Pro Val Gln Cys Ser Ser Ser His
        115                 120                 125

Asn Phe Thr Val Thr Arg Glu Ala Val Glu Ala Ala Tyr Gln Lys Ala
    130                 135                 140

Gln Glu Ala Asn Ile Asn Val Thr Gly Leu Ile Ile Thr Asn Pro Ser
145                 150                 155                 160

Asn Pro Leu Gly Thr Thr Leu Asp Ser Gln Thr Leu Gln Ser Leu Val
                165                 170                 175

Ile Phe Val Asn Asp Lys Thr Ile His Leu Val Cys Asp Glu Ile Tyr
            180                 185                 190

Ala Ala Thr Val Phe Ser Ser Pro Glu Phe Val Ser Ile Gly Glu Ile
        195                 200                 205

Ile Gln Glu Met Asp Val Asn Arg Asp Leu Ile His Ile Ile Tyr Ser
    210                 215                 220

Leu Ser Lys Asp Met Gly Leu Pro Gly Phe Arg Val Gly Ile Val Tyr
225                 230                 235                 240

Ser Tyr Asn Asp Gly Val Leu Ser Cys Gly Arg Arg Met Ser Ser Phe
                245                 250                 255

Gly Leu Val Ser Ser Gln Thr Gln Tyr Phe Leu Ala Thr Leu Leu Ser
            260                 265                 270

Asp Asp Glu Phe Val Asp Tyr Phe Leu Arg Glu Ser Ser Lys Arg Leu
        275                 280                 285

Ala Arg Arg His His Lys Leu Thr Arg Gly Leu Glu Gln Val Gly Ile
    290                 295                 300

Lys Cys Leu Lys Ser Asn Ala Gly Leu Phe Val Trp Met Asp Leu Arg
305                 310                 315                 320

Arg Leu Leu Glu Gly Pro Thr Ser Phe Asp Ala Glu Met Lys Leu Trp
                325                 330                 335

Arg Thr Ile Val Asn Asp Val Lys Leu Asn Val Ser Pro Gly Ser Ser
            340                 345                 350

Phe His Val Ala Glu Pro Gly Trp Phe Arg Val Cys Phe Ala
        355                 360                 365
```

(2) INFORMATION FOR SEQ ID NO: 7:

(i) SEQUENCE CHARACTERISTICS:
(A) LENGTH: 1096 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..1095

(xi) SEQUENCE DESCRIPTION: SEQ ID NO: 7:

```
CAG ATG GGC CTT GCC GAG AAT CAG CTT TGC TTT GAT TTG ATC GAA GAC       48
Gln Met Gly Leu Ala Glu Asn Gln Leu Cys Phe Asp Leu Ile Glu Asp
  1               5                  10                  15

TGG ATT CGC AAA AAT CCC TAT GCC TCC ATT TGT ACT GCT GAA GGA GTT       96
Trp Ile Arg Lys Asn Pro Tyr Ala Ser Ile Cys Thr Ala Glu Gly Val
             20                  25                  30

GAT GAG TTC AAG GAG ATT GCA AAC TTT CAA GAT TAT CAT GGC TTG CCA      144
Asp Glu Phe Lys Glu Ile Ala Asn Phe Gln Asp Tyr His Gly Leu Pro
         35                  40                  45

GAG TTT AGA AAG GCT GTG GCA AAG TTT ATG GGA AAA GTG AGA GGT GGA      192
```

-continued

```
Glu Phe Arg Lys Ala Val Ala Lys Phe Met Gly Lys Val Arg Gly Gly
     50                  55                  60

AGA GTA ACA TTT GAT CCA GAC CGT ATA GTC ATG GGC GGT GGA GTT ACA       240
Arg Val Thr Phe Asp Pro Asp Arg Ile Val Met Gly Gly Gly Val Thr
 65                  70                  75                  80

GGC GCA AAC GAG CAA ATC ATC TTC TGT TTA GCC GAC CCT GGC GAT GCT       288
Gly Ala Asn Glu Gln Ile Ile Phe Cys Leu Ala Asp Pro Gly Asp Ala
                 85                  90                  95

TTT CTT GTT CCC TCA CCT TAT TAT CCA GCA TTT GAC CGG GAC CTG GGA       336
Phe Leu Val Pro Ser Pro Tyr Tyr Pro Ala Phe Asp Arg Asp Leu Gly
            100                 105                 110

TGG CGC ACT GGA GGT GAA ATA GTT CCT GTT CCC TGT GAC AGC TCA ACC       384
Trp Arg Thr Gly Gly Glu Ile Val Pro Val Pro Cys Asp Ser Ser Thr
        115                 120                 125

AAT TTC CAG ATA ACC AGA GAT GCA TTG GAA GAA GCA TAT GAA AAA GCT       432
Asn Phe Gln Ile Thr Arg Asp Ala Leu Glu Glu Ala Tyr Glu Lys Ala
    130                 135                 140

CGA GAA GCC AAC ATT AAT ATT AAA GGC TTG ATC ATA ACA AAC CCT TCA       480
Arg Glu Ala Asn Ile Asn Ile Lys Gly Leu Ile Ile Thr Asn Pro Ser
145                 150                 155                 160

AAC CCA CTT GGC ATC ACC CTA GAC AGA GAT ACT CTT AAA AGC CTA GTG       528
Asn Pro Leu Gly Ile Thr Leu Asp Arg Asp Thr Leu Lys Ser Leu Val
                165                 170                 175

AGC TTC ATC GAT GAA AAG AAC ATT CAC TTT GTC TGC GAT GAA ATC TAT       576
Ser Phe Ile Asp Glu Lys Asn Ile His Phe Val Cys Asp Glu Ile Tyr
            180                 185                 190

GCT GCC ACT CTC TTC TGT CCA CCC AAG TTC GTA AGC GTC GCT GAA GTG       624
Ala Ala Thr Leu Phe Cys Pro Pro Lys Phe Val Ser Val Ala Glu Val
        195                 200                 205

ATC CAA GAA ATG GAC TGT AAT CTT GAT CTC ATC CAC ATT GTT TAC AGT       672
Ile Gln Glu Met Asp Cys Asn Leu Asp Leu Ile His Ile Val Tyr Ser
    210                 215                 220

TTG TCT AAG GAC ATG GGC CTC CCT GGC TTT AGG GTT GGC ATT GTT TAT       720
Leu Ser Lys Asp Met Gly Leu Pro Gly Phe Arg Val Gly Ile Val Tyr
225                 230                 235                 240

TCT TAT AAT GAT GCA GTT GTG AGT TGT ATC CGC AAG ATG TCA AGC TTC       768
Ser Tyr Asn Asp Ala Val Val Ser Cys Ile Arg Lys Met Ser Ser Phe
                245                 250                 255

GGT TTG GTA TCC TCA CAA ACT CAA TAT TTA CTC GCT TCA ATG CTT TCT       816
Gly Leu Val Ser Ser Gln Thr Gln Tyr Leu Leu Ala Ser Met Leu Ser
            260                 265                 270

GAT GAT GAA TTT GTG GAA AAG TTT CTA GCG GAA AGC TCA AAG AGG CTG       864
Asp Asp Glu Phe Val Glu Lys Phe Leu Ala Glu Ser Ser Lys Arg Leu
        275                 280                 285

GCA AAA AGG TAC CAT ATT TTC ACA AAG AGA CTT GAG AAA GTG GGG ATT       912
Ala Lys Arg Tyr His Ile Phe Thr Lys Arg Leu Glu Lys Val Gly Ile
    290                 295                 300

AAC TGC TTG AAG GGA AAT GCA GGT CTT TTC TTC TGG ATG GAT TTG CGA       960
Asn Cys Leu Lys Gly Asn Ala Gly Leu Phe Phe Trp Met Asp Leu Arg
305                 310                 315                 320

CAC CTC CTT CAA CAA GAA ACA GTT GAT GCC GAA ATG AAG CTA TGG GGC      1008
His Leu Leu Gln Gln Glu Thr Val Asp Ala Glu Met Lys Leu Trp Gly
                325                 330                 335

ACG ATT TTG AAC GAT GTG AAA CTT AAC GTT TCA CCA GGC TCT TCC TTT      1056
Thr Ile Leu Asn Asp Val Lys Leu Asn Val Ser Pro Gly Ser Ser Phe
            340                 345                 350

CAT TGC CAG GAG CCT GGT TGG TTC AGA GTC TGC TTC GCT G                1096
His Cys Gln Glu Pro Gly Trp Phe Arg Val Cys Phe Ala
        355                 360                 365
```

```
(2) INFORMATION FOR SEQ ID NO: 8:

     (i) SEQUENCE CHARACTERISTICS:
          (A) LENGTH: 365 amino acids
          (B) TYPE: amino acid
          (D) TOPOLOGY: linear

    (ii) MOLECULE TYPE: protein

    (xi) SEQUENCE DESCRIPTION: SEQ ID NO: 8:

Gln Met Gly Leu Ala Glu Asn Gln Leu Cys Phe Asp Leu Ile Glu Asp
  1               5                  10                  15

Trp Ile Arg Lys Asn Pro Tyr Ala Ser Ile Cys Thr Ala Glu Gly Val
             20                  25                  30

Asp Glu Phe Lys Glu Ile Ala Asn Phe Gln Asp Tyr His Gly Leu Pro
         35                  40                  45

Glu Phe Arg Lys Ala Val Ala Lys Phe Met Gly Lys Val Arg Gly Gly
     50                  55                  60

Arg Val Thr Phe Asp Pro Asp Arg Ile Val Met Gly Gly Gly Val Thr
 65                  70                  75                  80

Gly Ala Asn Glu Gln Ile Ile Phe Cys Leu Ala Asp Pro Gly Asp Ala
                 85                  90                  95

Phe Leu Val Pro Ser Pro Tyr Tyr Pro Ala Phe Asp Arg Asp Leu Gly
            100                 105                 110

Trp Arg Thr Gly Gly Glu Ile Val Pro Val Pro Cys Asp Ser Ser Thr
        115                 120                 125

Asn Phe Gln Ile Thr Arg Asp Ala Leu Glu Glu Ala Tyr Glu Lys Ala
    130                 135                 140

Arg Glu Ala Asn Ile Asn Ile Lys Gly Leu Ile Ile Thr Asn Pro Ser
145                 150                 155                 160

Asn Pro Leu Gly Ile Thr Leu Asp Arg Asp Thr Leu Lys Ser Leu Val
                165                 170                 175

Ser Phe Ile Asp Glu Lys Asn Ile His Phe Val Cys Asp Glu Ile Tyr
            180                 185                 190

Ala Ala Thr Leu Phe Cys Pro Pro Lys Phe Val Ser Val Ala Glu Val
        195                 200                 205

Ile Gln Glu Met Asp Cys Asn Leu Asp Leu Ile His Ile Val Tyr Ser
    210                 215                 220

Leu Ser Lys Asp Met Gly Leu Pro Gly Phe Arg Val Gly Ile Val Tyr
225                 230                 235                 240

Ser Tyr Asn Asp Ala Val Val Ser Cys Ile Arg Lys Met Ser Ser Phe
                245                 250                 255

Gly Leu Val Ser Ser Gln Thr Gln Tyr Leu Leu Ala Ser Met Leu Ser
            260                 265                 270

Asp Asp Glu Phe Val Glu Lys Phe Leu Ala Glu Ser Ser Lys Arg Leu
        275                 280                 285

Ala Lys Arg Tyr His Ile Phe Thr Lys Arg Leu Glu Lys Val Gly Ile
    290                 295                 300

Asn Cys Leu Lys Gly Asn Ala Gly Leu Phe Phe Trp Met Asp Leu Arg
305                 310                 315                 320

His Leu Leu Gln Gln Glu Thr Val Asp Ala Glu Met Lys Leu Trp Gly
                325                 330                 335

Thr Ile Leu Asn Asp Val Lys Leu Asn Val Ser Pro Gly Ser Ser Phe
            340                 345                 350

His Cys Gln Glu Pro Gly Trp Phe Arg Val Cys Phe Ala
```

-continued

```
        355                 360                 365

(2) INFORMATION FOR SEQ ID NO: 9:

     (i) SEQUENCE CHARACTERISTICS:
          (A) LENGTH: 1113 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 1..1113

    (xi) SEQUENCE DESCRIPTION: SEQ ID NO: 9:

CAG ATG GGA TTT GGG GAA AAT CTG CTT TGC TTT GAT TTA GTT CAA GAA        48
Gln Met Gly Phe Gly Glu Asn Leu Leu Cys Phe Asp Leu Val Gln Glu
  1               5                  10                  15

TGG GTC TTA AGC AAC CCA GAA GCC TCT ATC TGC ACT GCC GAA GGT ATA        96
Trp Val Leu Ser Asn Pro Glu Ala Ser Ile Cys Thr Ala Glu Gly Ile
             20                  25                  30

AGT GAT TTC AGA GAT ATC GCT ATC TTT CAG GAT TAT CAC GGC TTG CCA       144
Ser Asp Phe Arg Asp Ile Ala Ile Phe Gln Asp Tyr His Gly Leu Pro
         35                  40                  45

GAG TTC AGA AAT GCT GTT GCA AAT TTT ATG GCA AGA GTG AGA GGG AAT       192
Glu Phe Arg Asn Ala Val Ala Asn Phe Met Ala Arg Val Arg Gly Asn
     50                  55                  60

AGA GTC AAA TAC GAC CCT GAT CGA ATT GTT ATG AGC GGT GGA GCA ACC       240
Arg Val Lys Tyr Asp Pro Asp Arg Ile Val Met Ser Gly Gly Ala Thr
 65                  70                  75                  80

GGA GCA CAT GAG ACG GTT GCC TTT TGT TTG GCT GAT CCC GGT GAA GCA       288
Gly Ala His Glu Thr Val Ala Phe Cys Leu Ala Asp Pro Gly Glu Ala
                 85                  90                  95

TTT TTG GGT GCC ACT CCT TAC TAT CCA GGA TTT GGT CGA GAT TTG AGA       336
Phe Leu Gly Ala Thr Pro Tyr Tyr Pro Gly Phe Gly Arg Asp Leu Arg
            100                 105                 110

TGG AGA ACA GGA GTT CAA CTT TTT CCA GTT GTG TGT GAC AGT TCT AAC       384
Trp Arg Thr Gly Val Gln Leu Phe Pro Val Val Cys Asp Ser Ser Asn
        115                 120                 125

AAT TTC AAG ATT ACA AGA GAA GCC GTG GAA GCA GCA TAT GAA AAA GCT       432
Asn Phe Lys Ile Thr Arg Glu Ala Val Glu Ala Ala Tyr Glu Lys Ala
    130                 135                 140

CAA GAA GAC CAC ATC AGA ATC AAG GGT TTG GTC CTC ACA AAT CCA TCG       480
Gln Glu Asp His Ile Arg Ile Lys Gly Leu Val Leu Thr Asn Pro Ser
145                 150                 155                 160

AAC CCG CTG GGG ACT TGT TTG GAC AGA GAA ACA CTA AGA AGT TTA GTA       528
Asn Pro Leu Gly Thr Cys Leu Asp Arg Glu Thr Leu Arg Ser Leu Val
                165                 170                 175

AGC TTC ATT AAT GAA AAG AAC ATC CAC TTA GTC TGC GAC GAG ATT TAT       576
Ser Phe Ile Asn Glu Lys Asn Ile His Leu Val Cys Asp Glu Ile Tyr
            180                 185                 190

GCT GCC ACA ATC TTC ATG GGC CAG CCC GAT TTC ATT AGC ATC TCT GAA       624
Ala Ala Thr Ile Phe Met Gly Gln Pro Asp Phe Ile Ser Ile Ser Glu
        195                 200                 205

ATT ATA GAA GAA GAT ATT CAC TGC AAT CGC AAT CTC ATC CAC CTT GTT       672
Ile Ile Glu Glu Asp Ile His Cys Asn Arg Asn Leu Ile His Leu Val
    210                 215                 220

TAC AGT CTT TCA AAG GAT CTG GGG TTC CCA GGC TTT AGG GTC GGC ATT       720
Tyr Ser Leu Ser Lys Asp Leu Gly Phe Pro Gly Phe Arg Val Gly Ile
225                 230                 235                 240
```

-continued

```
ATA TAC TCA TAC AAC GAT ACA GTT GTG AGT TGC GCC TGC AAA ATG TCA      768
Ile Tyr Ser Tyr Asn Asp Thr Val Val Ser Cys Ala Cys Lys Met Ser
                245                 250                 255

AGC TTT GGA CTT GTA TCA TCA CAA ACT CAA CAT TTA ATC GCT TCA ATG      816
Ser Phe Gly Leu Val Ser Ser Gln Thr Gln His Leu Ile Ala Ser Met
            260                 265                 270

TTA TCA GAT GAT GAA TTT GTG GAT AGG TTC ATT ACT GAG AGT GCT AAA      864
Leu Ser Asp Asp Glu Phe Val Asp Arg Phe Ile Thr Glu Ser Ala Lys
        275                 280                 285

AGG CTT GCA AAA AGG CAC AGA GCC TTC ACA TGG GGG CTA TCT CAA GTA      912
Arg Leu Ala Lys Arg His Arg Ala Phe Thr Trp Gly Leu Ser Gln Val
    290                 295                 300

GGC ATT GGT TGT TTG AAG AGC AAT GCG GGG CTA TTT TTC TGG ATG GAT      960
Gly Ile Gly Cys Leu Lys Ser Asn Ala Gly Leu Phe Phe Trp Met Asp
305                 310                 315                 320

TTG CAT CAT CTC CTC AAG GAG CAA ACT GAT GAA GCA GAG ATA GAA CTG     1008
Leu His His Leu Leu Lys Glu Gln Thr Asp Glu Ala Glu Ile Glu Leu
                325                 330                 335

TGG AAA GTG ATA ATC AAC GAA GTT AAA TTA AAT GTT TCT CCG GGT TCT     1056
Trp Lys Val Ile Ile Asn Glu Val Lys Leu Asn Val Ser Pro Gly Ser
            340                 345                 350

TCC TTT CAT TGC GCT AAT CCA GGA TGG TTT CGG GTT TGT TTC GCC AAC     1104
Ser Phe His Cys Ala Asn Pro Gly Trp Phe Arg Val Cys Phe Ala Asn
        355                 360                 365

ATG GAC GAA                                                         1113
Met Asp Glu
    370
```

(2) INFORMATION FOR SEQ ID NO: 10:

(i) SEQUENCE CHARACTERISTICS:
(A) LENGTH: 371 amino acids
(B) TYPE: amino acid
(D) TOPOLOGY: linear (ii) MOLECULE TYPE: protein (xi) SEQUENCE DESCRIPTION: SEQ ID NO: 10:

```
Gln Met Gly Phe Gly Glu Asn Leu Leu Cys Phe Asp Leu Val Gln Glu
  1               5                  10                  15

Trp Val Leu Ser Asn Pro Glu Ala Ser Ile Cys Thr Ala Glu Gly Ile
             20                  25                  30

Ser Asp Phe Arg Asp Ile Ala Ile Phe Gln Asp Tyr His Gly Leu Pro
         35                  40                  45

Glu Phe Arg Asn Ala Val Ala Asn Phe Met Ala Arg Val Arg Gly Asn
     50                  55                  60

Arg Val Lys Tyr Asp Pro Asp Arg Ile Val Met Ser Gly Gly Ala Thr
 65                  70                  75                  80

Gly Ala His Glu Thr Val Ala Phe Cys Leu Ala Asp Pro Gly Glu Ala
                 85                  90                  95

Phe Leu Gly Ala Thr Pro Tyr Tyr Pro Gly Phe Gly Arg Asp Leu Arg
            100                 105                 110

Trp Arg Thr Gly Val Gln Leu Phe Pro Val Val Cys Asp Ser Ser Asn
        115                 120                 125

Asn Phe Lys Ile Thr Arg Glu Ala Val Glu Ala Ala Tyr Glu Lys Ala
    130                 135                 140

Gln Glu Asp His Ile Arg Ile Lys Gly Leu Val Leu Thr Asn Pro Ser
145                 150                 155                 160

Asn Pro Leu Gly Thr Cys Leu Asp Arg Glu Thr Leu Arg Ser Leu Val
```

-continued

```
                165                 170                 175

Ser Phe Ile Asn Glu Lys Asn Ile His Leu Val Cys Asp Glu Ile Tyr
            180                 185                 190

Ala Ala Thr Ile Phe Met Gly Gln Pro Asp Phe Ile Ser Ile Ser Glu
        195                 200                 205

Ile Ile Glu Glu Asp Ile His Cys Asn Arg Asn Leu Ile His Leu Val
    210                 215                 220

Tyr Ser Leu Ser Lys Asp Leu Gly Phe Pro Gly Phe Arg Val Gly Ile
225                 230                 235                 240

Ile Tyr Ser Tyr Asn Asp Thr Val Val Ser Cys Ala Cys Lys Met Ser
                245                 250                 255

Ser Phe Gly Leu Val Ser Ser Gln Thr Gln His Leu Ile Ala Ser Met
            260                 265                 270

Leu Ser Asp Asp Glu Phe Val Asp Arg Phe Ile Thr Glu Ser Ala Lys
        275                 280                 285

Arg Leu Ala Lys Arg His Arg Ala Phe Thr Trp Gly Leu Ser Gln Val
    290                 295                 300

Gly Ile Gly Cys Leu Lys Ser Asn Ala Gly Leu Phe Phe Trp Met Asp
305                 310                 315                 320

Leu His His Leu Leu Lys Glu Gln Thr Asp Glu Ala Glu Ile Glu Leu
                325                 330                 335

Trp Lys Val Ile Ile Asn Glu Val Lys Leu Asn Val Ser Pro Gly Ser
            340                 345                 350

Ser Phe His Cys Ala Asn Pro Gly Trp Phe Arg Val Cys Phe Ala Asn
        355                 360                 365

Met Asp Glu
    370
```

(2) INFORMATION FOR SEQ ID NO: 11:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO: 11:

TAYTTYGAYG GNTGGAARGC 20

(2) INFORMATION FOR SEQ ID NO: 12:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO: 12:

TCRTCCATRT TNGCRAARCA 20

(2) INFORMATION FOR SEQ ID NO: 13:

(i) SEQUENCE CHARACTERISTICS:
(A) LENGTH: 20 base pairs
(B) TYPE: nucleic acid (C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO: 13:

CARATGGGNY TNGCNGARAA 20

(2) INFORMATION FOR SEQ ID NO: 14:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO: 14:

GCRAARCANA CNCKRAACCA 20

(2) INFORMATION FOR SEQ ID NO: 15:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO: 15:

ACNCKRAACC ANCCNGGYTC 20

(2) INFORMATION FOR SEQ ID NO: 16:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO: 16:

GCTCTAGATA YTTYGAYGGN TGGAARGC 28

(2) INFORMATION FOR SEQ ID NO: 17:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO: 17:

GCGAATTCRT CCATRTTNGC RAARCA 26

(2) INFORMATION FOR SEQ ID NO: 18:

(i) SEQUENCE CHARACTERISTICS:
(A) LENGTH: 26 base pairs

-continued

```
        (B) TYPE: nucleic acid
        (C) STRANDEDNESS: single
        (D) TOPOLOGY: linear

   (ii) MOLECULE TYPE: other nucleic acid
        (A) DESCRIPTION: /desc = "primer"

   (xi) SEQUENCE DESCRIPTION: SEQ ID NO: 18:

CCTGATCARA TGGGNYTNGC NGARAA                                          26


(2) INFORMATION FOR SEQ ID NO: 19:

    (i) SEQUENCE CHARACTERISTICS:
        (A) LENGTH: 27 base pairs
        (B) TYPE: nucleic acid
        (C) STRANDEDNESS: single
        (D) TOPOLOGY: linear

   (ii) MOLECULE TYPE: other nucleic acid
        (A) DESCRIPTION: /desc = "primer"

   (xi) SEQUENCE DESCRIPTION: SEQ ID NO: 19:

CTCTGCAGCR AARCANACNC KRAACCA                                         27
```